(12) United States Patent
Swett et al.

(10) Patent No.: US 10,203,295 B2
(45) Date of Patent: Feb. 12, 2019

(54) METHODS FOR IN SITU MONITORING AND CONTROL OF DEFECT FORMATION OR HEALING

(71) Applicant: Lockheed Martin Corporation, Bethesda, MD (US)

(72) Inventors: Jacob L. Swett, Redwood City, CA (US); Peter V. Bedworth, Los Gatos, CA (US)

(73) Assignee: Lockheed Martin Corporation, Bethesda, MD (US)

(*) Notice: Subject to any disclaimer, the term of this patent is extended or adjusted under 35 U.S.C. 154(b) by 306 days.

(21) Appl. No.: 15/099,056

(22) Filed: Apr. 14, 2016

(65) Prior Publication Data

US 2017/0299537 A1    Oct. 19, 2017

(51) Int. Cl.
    *G01V 3/38*    (2006.01)
    *G01N 27/20*   (2006.01)
    (Continued)

(52) U.S. Cl.
    CPC ........... *G01N 27/20* (2013.01); *G01N 23/225* (2013.01); *G01N 25/72* (2013.01); *G01N 27/041* (2013.01);
    (Continued)

(58) Field of Classification Search
    CPC ... G01V 3/38; G01V 3/26; G01V 3/30; G01V 3/32; G01V 3/28; G01V 3/20; G01V 3/18;
    (Continued)

(56) References Cited

U.S. PATENT DOCUMENTS 2,187,417 A    1/1940 Doble
3,024,153 A    3/1962 Kennedy
(Continued)

FOREIGN PATENT DOCUMENTS

CA    2037988    9/1992
CA    2411935    12/2002
(Continued)

OTHER PUBLICATIONS

Allen et al., "Craters on silicon surfaces created by gas cluster ion impacts," Journal of Applied Physics, 92(7): 3671-3678 (Oct. 2002).

(Continued)

*Primary Examiner* — Jermele M Hollington
*Assistant Examiner* — Taqi Nasir
(74) *Attorney, Agent, or Firm* — Foley & Lardner LLP

(57) ABSTRACT

Production of perforated two-dimensional materials with holes of a desired size range, a narrow size distribution, and a high and uniform density remains a challenge, at least partially, due to physical and chemical inconsistencies from sheet-to-sheet of the two-dimensional material and surface contamination. This disclosure describes methods for monitoring and adjusting perforation or healing conditions in real-time to address inter- and intra-sheet variability. In situ or substantially simultaneous feedback on defect production or healing may be provided either locally or globally on a graphene or other two-dimensional sheet. The feedback data can be used to adjust perforation or healing parameters, such as the total dose or efficacy of the perforating radiation, to achieve the desired defect state.

38 Claims, 7 Drawing Sheets

(51) Int. Cl.
*G01N 25/72* (2006.01)
*G01N 27/04* (2006.01)
*G01N 33/00* (2006.01)
*G01N 23/225* (2018.01)
*B82Y 40/00* (2011.01)

(52) U.S. Cl.
CPC .............. *G01N 33/00* (2013.01); *B82Y 40/00* (2013.01); *G01N 2033/0095* (2013.01); *G01N 2223/603* (2013.01); *G01N 2223/6462* (2013.01)

(58) Field of Classification Search
CPC . G01V 13/00; G01V 3/24; G01V 3/34; G01V 3/14; G01V 11/00
USPC ....... 324/324, 333, 338, 346, 351, 355, 368, 324/372, 221, 303, 366, 386, 754.1, 324/754.11, 754.24
See application file for complete search history.

(56) References Cited

U.S. PATENT DOCUMENTS

| | | |
|---|---|---|
| 3,303,085 A | 2/1967 | Price et al. |
| 3,501,831 A | 3/1970 | Gordon |
| 3,593,854 A | 7/1971 | Swank |
| 3,692,059 A | 9/1972 | Ice, Jr. |
| 3,701,433 A | 10/1972 | Krakauer et al. |
| 3,802,972 A | 4/1974 | Fleischer et al. |
| 4,073,732 A | 2/1978 | Lauer et al. |
| 4,159,954 A | 7/1979 | Gangemi |
| 4,162,220 A | 7/1979 | Servas |
| 4,277,344 A | 7/1981 | Cadotte |
| 4,303,530 A | 12/1981 | Shah et al. |
| 4,743,371 A | 5/1988 | Servas et al. |
| 4,855,058 A | 8/1989 | Holland et al. |
| 4,880,440 A | 11/1989 | Perrin |
| 4,889,626 A | 12/1989 | Browne |
| 4,891,134 A | 1/1990 | Vcelka |
| 4,925,560 A | 5/1990 | Sorrick |
| 4,935,207 A | 6/1990 | Stanbro et al. |
| 4,976,858 A | 12/1990 | Kadoya |
| 5,052,444 A | 10/1991 | Messerly et al. |
| 5,080,770 A | 1/1992 | Culkin |
| 5,082,476 A | 1/1992 | Kahlbaugh et al. |
| 5,156,628 A | 10/1992 | Kranz |
| 5,182,111 A | 1/1993 | Aebischer et al. |
| 5,185,086 A | 2/1993 | Kaali et al. |
| 5,201,767 A | 4/1993 | Caldarise et al. |
| 5,244,981 A | 9/1993 | Seidner et al. |
| 5,314,492 A | 5/1994 | Hamilton et al. |
| 5,314,960 A | 5/1994 | Spinelli et al. |
| 5,314,961 A | 5/1994 | Anton et al. |
| 5,331,067 A | 7/1994 | Seidner et al. |
| 5,344,454 A | 9/1994 | Clarke et al. |
| 5,371,147 A | 12/1994 | Spinelli et al. |
| 5,425,858 A | 6/1995 | Farmer |
| 5,480,449 A | 1/1996 | Hamilton et al. |
| 5,514,181 A | 5/1996 | Light et al. |
| 5,516,522 A | 5/1996 | Peyman et al. |
| 5,549,697 A | 8/1996 | Caldarise |
| 5,562,944 A | 10/1996 | Kafrawy |
| 5,565,210 A | 10/1996 | Rosenthal et al. |
| 5,580,530 A | 12/1996 | Kowatsch et al. |
| 5,595,621 A | 1/1997 | Light et al. |
| 5,636,437 A | 6/1997 | Kaschmitter et al. |
| 5,639,275 A | 6/1997 | Baetge et al. |
| 5,641,323 A | 6/1997 | Caldarise |
| 5,658,334 A | 8/1997 | Caldarise et al. |
| 5,662,158 A | 9/1997 | Caldarise |
| 5,665,118 A | 9/1997 | Lasalle et al. |
| 5,671,897 A | 9/1997 | Ogg et al. |
| 5,679,232 A | 10/1997 | Fedor et al. |
| 5,679,249 A | 10/1997 | Fendya et al. |
| 5,687,788 A | 11/1997 | Caldarise et al. |
| 5,700,477 A | 12/1997 | Rosenthal et al. |
| 5,713,410 A | 2/1998 | Lasalle et al. |
| 5,716,412 A | 2/1998 | Decarlo et al. |
| 5,716,414 A | 2/1998 | Caldarise |
| 5,725,586 A | 3/1998 | Sommerich |
| 5,731,360 A | 3/1998 | Pekala et al. |
| 5,733,503 A | 3/1998 | Kowatsch et al. |
| 5,746,272 A | 5/1998 | Mastrorio et al. |
| 5,782,286 A | 7/1998 | Sommerich |
| 5,782,289 A | 7/1998 | Mastrorio et al. |
| 5,788,916 A | 8/1998 | Caldarise |
| 5,800,828 A | 9/1998 | Dionne et al. |
| 5,808,312 A | 9/1998 | Fukuda |
| 5,868,727 A | 2/1999 | Barr et al. |
| 5,897,592 A | 4/1999 | Caldarise et al. |
| 5,902,762 A | 5/1999 | Mercuri et al. |
| 5,906,234 A | 5/1999 | Mastrorio et al. |
| 5,910,172 A | 6/1999 | Penenberg |
| 5,910,173 A | 6/1999 | Decarlo et al. |
| 5,913,998 A | 6/1999 | Butler et al. |
| 5,922,304 A | 7/1999 | Unger |
| 5,925,247 A | 7/1999 | Huebbel |
| 5,932,185 A | 8/1999 | Pekala et al. |
| 5,935,084 A | 8/1999 | Southworth |
| 5,935,172 A | 8/1999 | Ochoa et al. |
| 5,954,937 A | 9/1999 | Farmer |
| 5,974,973 A | 11/1999 | Tittgemeyer |
| 5,976,555 A | 11/1999 | Liu et al. |
| 5,980,718 A | 11/1999 | Van Konynenburg et al. |
| 6,008,431 A | 12/1999 | Caldarise et al. |
| 6,013,080 A | 1/2000 | Khalili |
| 6,022,509 A | 2/2000 | Matthews et al. |
| 6,052,608 A | 4/2000 | Young et al. |
| 6,080,393 A | 6/2000 | Liu et al. |
| 6,093,209 A | 7/2000 | Sanders |
| 6,139,585 A | 10/2000 | Li |
| 6,152,882 A | 11/2000 | Prutchi |
| 6,156,323 A | 12/2000 | Verdicchio et al. |
| 6,193,956 B1 | 2/2001 | Liu et al. |
| 6,209,621 B1 | 4/2001 | Treacy |
| 6,213,124 B1 | 4/2001 | Butterworth |
| 6,228,123 B1 | 5/2001 | Dezzani |
| 6,264,699 B1 | 7/2001 | Noiles et al. |
| 6,292,704 B1 | 9/2001 | Malonek et al. |
| 6,309,532 B1 | 10/2001 | Tran et al. |
| 6,346,187 B1 | 2/2002 | Tran et al. |
| 6,375,014 B1 | 4/2002 | Garcera et al. |
| 6,426,214 B1 | 7/2002 | Butler et al. |
| 6,454,095 B1 | 9/2002 | Brisebois et al. |
| 6,455,115 B1 | 9/2002 | Demeyer |
| 6,461,622 B2 | 10/2002 | Liu et al. |
| 6,462,935 B1 | 10/2002 | Shiue et al. |
| 6,521,865 B1 | 2/2003 | Jones et al. |
| 6,532,386 B2 | 3/2003 | Sun et al. |
| 6,544,316 B2 | 4/2003 | Baker et al. |
| 6,580,598 B2 | 6/2003 | Shiue et al. |
| 6,654,229 B2 | 11/2003 | Yanagisawa et al. |
| 6,659,298 B2 | 12/2003 | Wong |
| 6,660,150 B2 | 12/2003 | Conlan et al. |
| 6,661,643 B2 | 12/2003 | Shiue et al. |
| 6,686,437 B2 | 2/2004 | Buchman et al. |
| 6,692,627 B1 | 2/2004 | Russell et al. |
| 6,695,880 B1 | 2/2004 | Roffman et al. |
| 6,699,684 B2 | 3/2004 | Ho et al. |
| 6,719,740 B2 | 4/2004 | Burnett et al. |
| 6,905,612 B2 | 6/2005 | Dorian et al. |
| 6,924,190 B2 | 8/2005 | Dennison |
| 7,014,829 B2 | 3/2006 | Yanagisawa et al. |
| 7,071,406 B2 | 7/2006 | Smalley et al. |
| 7,092,753 B2 | 8/2006 | Darvish et al. |
| 7,138,042 B2 | 11/2006 | Tran et al. |
| 7,171,263 B2 | 1/2007 | Darvish et al. |
| 7,175,783 B2 | 2/2007 | Curran |
| 7,179,419 B2 | 2/2007 | Lin et al. |
| 7,190,997 B1 | 3/2007 | Darvish et al. |
| 7,267,753 B2 | 9/2007 | Anex et al. |
| 7,306,768 B2 | 12/2007 | Chiga |
| 7,357,255 B2 | 4/2008 | Ginsberg et al. |
| 7,374,677 B2 | 5/2008 | McLaughlin et al. |

(56) References Cited

U.S. PATENT DOCUMENTS

| | | | |
|---|---|---|---|
| 7,381,707 B2 | 6/2008 | Lin et al. |
| 7,382,601 B2 | 6/2008 | Yoshimitsu |
| 7,434,692 B2 | 10/2008 | Ginsberg et al. |
| 7,452,547 B2 | 11/2008 | Lambino et al. |
| 7,459,121 B2 | 12/2008 | Liang et al. |
| 7,460,907 B1 | 12/2008 | Darvish et al. |
| 7,476,222 B2 | 1/2009 | Sun et al. |
| 7,477,939 B2 | 1/2009 | Sun et al. |
| 7,477,940 B2 | 1/2009 | Sun et al. |
| 7,477,941 B2 | 1/2009 | Sun et al. |
| 7,479,133 B2 | 1/2009 | Sun et al. |
| 7,505,250 B2 | 3/2009 | Cho et al. |
| 7,531,094 B2 | 5/2009 | McLaughlin et al. |
| 7,600,567 B2 | 10/2009 | Christopher et al. |
| 7,631,764 B2 | 12/2009 | Ginsberg et al. |
| 7,650,805 B2 | 1/2010 | Nauseda et al. |
| 7,674,477 B1 | 3/2010 | Schmid et al. |
| 7,706,128 B2 | 4/2010 | Bourcier |
| 7,761,809 B2 | 7/2010 | Bukovec et al. |
| 7,786,086 B2 | 8/2010 | Reches et al. |
| 7,866,475 B2 | 1/2011 | Doskoczynski et al. |
| 7,875,293 B2 | 1/2011 | Shults et al. |
| 7,935,331 B2 | 5/2011 | Lin |
| 7,935,416 B2 | 5/2011 | Yang et al. |
| 7,943,167 B2 | 5/2011 | Kulkarni et al. |
| 7,960,708 B2 | 6/2011 | Wolfe et al. |
| 7,998,246 B2 | 8/2011 | Liu et al. |
| 8,109,893 B2 | 2/2012 | Lande |
| 8,147,599 B2 | 4/2012 | McAlister |
| 8,262,943 B2 | 9/2012 | Meng et al. |
| 8,278,106 B2 | 10/2012 | Martinson et al. |
| 8,308,702 B2 | 11/2012 | Batchvarova et al. |
| 8,316,865 B2 | 11/2012 | Ochs et al. |
| 8,329,476 B2 | 12/2012 | Pitkanen et al. |
| 8,354,296 B2 | 1/2013 | Dimitrakopoulos et al. |
| 8,361,321 B2 | 1/2013 | Stetson et al. |
| 8,449,504 B2 | 5/2013 | Carter et al. |
| 8,471,562 B2 * | 6/2013 | Knizhnik ............... G01V 3/18 |
| | | 324/346 |
| 8,475,689 B2 | 7/2013 | Sun et al. |
| 8,506,807 B2 | 8/2013 | Lee et al. |
| 8,512,669 B2 | 8/2013 | Hauck |
| 8,513,324 B2 | 8/2013 | Scales et al. |
| 8,535,726 B2 | 9/2013 | Dai et al. |
| 8,592,291 B2 | 11/2013 | Shi et al. |
| 8,617,411 B2 | 12/2013 | Singh |
| 8,666,471 B2 | 3/2014 | Rogers et al. |
| 8,686,249 B1 | 4/2014 | Whitaker et al. |
| 8,697,230 B2 | 4/2014 | Ago et al. |
| 8,698,481 B2 | 4/2014 | Lieber et al. |
| 8,715,329 B2 | 5/2014 | Robinson et al. |
| 8,721,074 B2 | 5/2014 | Pugh et al. |
| 8,734,421 B2 | 5/2014 | Sun et al. |
| 8,744,567 B2 | 6/2014 | Fassih et al. |
| 8,751,015 B2 | 6/2014 | Frewin et al. |
| 8,753,468 B2 | 6/2014 | Caldwell et al. |
| 8,759,153 B2 | 6/2014 | Elian et al. |
| 8,808,257 B2 | 8/2014 | Pugh et al. |
| 8,828,211 B2 | 9/2014 | Garaj et al. |
| 8,840,552 B2 | 9/2014 | Brauker et al. |
| 8,857,983 B2 | 10/2014 | Pugh et al. |
| 8,861,821 B2 | 10/2014 | Osumi |
| 8,894,201 B2 | 11/2014 | Pugh et al. |
| 8,940,552 B2 | 1/2015 | Pugh et al. |
| 8,950,862 B2 | 2/2015 | Pugh et al. |
| 8,974,055 B2 | 3/2015 | Pugh et al. |
| 8,975,121 B2 | 3/2015 | Pugh et al. |
| 8,979,978 B2 | 3/2015 | Miller et al. |
| 8,986,932 B2 | 3/2015 | Turner et al. |
| 8,993,234 B2 | 3/2015 | Turner et al. |
| 8,993,327 B2 | 3/2015 | McKnight et al. |
| 9,014,639 B2 | 4/2015 | Pugh et al. |
| 9,017,937 B1 | 4/2015 | Turner et al. |
| 9,023,220 B2 | 5/2015 | Zurutuza et al. |
| 9,028,663 B2 | 5/2015 | Stetson et al. |
| 9,035,282 B2 | 5/2015 | Dimitrakopoulos et al. |
| 9,045,847 B2 | 6/2015 | Batchvarova et al. |
| 9,050,452 B2 | 6/2015 | Sun et al. |
| 9,052,533 B2 | 6/2015 | Pugh et al. |
| 9,056,282 B2 | 6/2015 | Miller et al. |
| 9,062,180 B2 | 6/2015 | Scales et al. |
| 9,067,811 B1 | 6/2015 | Bennett et al. |
| 9,070,615 B2 | 6/2015 | Elian et al. |
| 9,075,009 B2 | 7/2015 | Kim et al. |
| 9,080,267 B2 | 7/2015 | Batchvarova et al. |
| 9,095,823 B2 | 8/2015 | Fleming |
| 9,096,050 B2 | 8/2015 | Bedell et al. |
| 9,096,437 B2 | 8/2015 | Tour et al. |
| 9,102,111 B2 | 8/2015 | Pugh et al. |
| 9,108,158 B2 | 8/2015 | Yu et al. |
| 9,110,310 B2 | 8/2015 | Pugh et al. |
| 9,125,715 B2 | 9/2015 | Pugh et al. |
| 9,134,546 B2 | 9/2015 | Pugh et al. |
| 9,170,646 B2 | 10/2015 | Toner et al. |
| 9,185,486 B2 | 11/2015 | Pugh |
| 9,193,587 B2 | 11/2015 | Bennett |
| 9,195,075 B2 | 11/2015 | Pugh et al. |
| 9,225,375 B2 | 12/2015 | Pugh et al. |
| 9,388,048 B1 | 7/2016 | Zhou et al. |
| 9,425,709 B2 | 8/2016 | Hayashi et al. |
| 9,437,370 B2 | 9/2016 | Chen et al. |
| 9,463,421 B2 | 10/2016 | Fleming |
| 9,505,192 B2 | 11/2016 | Stoltenberg et al. |
| 9,545,600 B2 | 1/2017 | Miller et al. |
| 9,567,224 B2 | 2/2017 | Bedworth |
| 9,572,918 B2 | 2/2017 | Bachmann et al. |
| 9,592,475 B2 | 3/2017 | Stoltenberg et al. |
| 9,610,546 B2 | 4/2017 | Sinton et al. |
| 9,708,640 B2 | 7/2017 | Wu et al. |
| 9,713,794 B2 | 7/2017 | Choi et al. |
| 9,742,001 B2 | 8/2017 | Zhamu et al. |
| 9,870,895 B2 | 1/2018 | Bedworth |
| 10,017,852 B2 | 7/2018 | Heise |
| 2001/0036556 A1 | 11/2001 | Jen |
| 2001/0047157 A1 | 11/2001 | Burnett et al. |
| 2001/0055597 A1 | 12/2001 | Liu et al. |
| 2002/0079004 A1 | 6/2002 | Sato et al. |
| 2002/0079054 A1 | 6/2002 | Nakatani |
| 2002/0104435 A1 | 8/2002 | Baker et al. |
| 2002/0115957 A1 | 8/2002 | Sun et al. |
| 2002/0117659 A1 | 8/2002 | Lieber et al. |
| 2002/0183682 A1 | 12/2002 | Darvish et al. |
| 2002/0183686 A1 | 12/2002 | Darvish et al. |
| 2003/0052354 A1 | 3/2003 | Dennison |
| 2003/0134281 A1 | 7/2003 | Evans |
| 2003/0138777 A1 | 7/2003 | Evans |
| 2003/0146221 A1 | 8/2003 | Lauer et al. |
| 2003/0159985 A1 | 8/2003 | Siwy et al. |
| 2004/0018583 A1 | 1/2004 | Ho et al. |
| 2004/0035787 A1 | 2/2004 | Tanga et al. |
| 2004/0061253 A1 | 4/2004 | Kleinmeyer et al. |
| 2004/0063097 A1 | 4/2004 | Evans |
| 2004/0099324 A1 | 5/2004 | Fraser et al. |
| 2004/0111968 A1 | 6/2004 | Day et al. |
| 2004/0112865 A1 | 6/2004 | McCullough et al. |
| 2004/0121488 A1 | 6/2004 | Chang et al. |
| 2004/0142463 A1 | 7/2004 | Walker et al. |
| 2004/0185730 A1 | 9/2004 | Lambino et al. |
| 2004/0193043 A1 | 9/2004 | Duchon et al. |
| 2004/0199243 A1 | 10/2004 | Yodfat |
| 2004/0208796 A1 | 10/2004 | Chiga |
| 2004/0217036 A1 | 11/2004 | Ginsberg et al. |
| 2004/0241214 A1 | 12/2004 | Kirkwood et al. |
| 2004/0251136 A1 | 12/2004 | Lean et al. |
| 2005/0004508 A1 | 1/2005 | Sun et al. |
| 2005/0004509 A1 | 1/2005 | Sun et al. |
| 2005/0004550 A1 | 1/2005 | Sun et al. |
| 2005/0010161 A1 | 1/2005 | Sun et al. |
| 2005/0010192 A1 | 1/2005 | Sun et al. |
| 2005/0015042 A1 | 1/2005 | Sun et al. |
| 2005/0053563 A1 | 3/2005 | Manissier et al. |
| 2005/0112078 A1 | 5/2005 | Boddupalli et al. |
| 2005/0126966 A1 | 6/2005 | Tanida et al. |
| 2005/0129633 A1 | 6/2005 | Lin |

(56) References Cited

U.S. PATENT DOCUMENTS

| | | |
|---|---|---|
| 2005/0148996 A1 | 7/2005 | Sun et al. |
| 2005/0170089 A1 | 8/2005 | Lashmore et al. |
| 2005/0189673 A1 | 9/2005 | Klug et al. |
| 2005/0226834 A1 | 10/2005 | Lambino et al. |
| 2005/0238730 A1 | 10/2005 | Le Fur et al. |
| 2006/0005381 A1 | 1/2006 | Nishi et al. |
| 2006/0036332 A1 | 2/2006 | Jennings |
| 2006/0073370 A1 | 4/2006 | Krusic et al. |
| 2006/0093885 A1 | 5/2006 | Krusic et al. |
| 2006/0121279 A1 | 6/2006 | Petrik |
| 2006/0151382 A1 | 7/2006 | Petrik |
| 2006/0166347 A1 | 7/2006 | Faulstich et al. |
| 2006/0180604 A1 | 8/2006 | Ginsberg et al. |
| 2006/0222701 A1 | 10/2006 | Kulkarni et al. |
| 2006/0253078 A1 | 11/2006 | Wu et al. |
| 2007/0004640 A1 | 1/2007 | Lin et al. |
| 2007/0032054 A1 | 2/2007 | Ramaswamy et al. |
| 2007/0056894 A1 | 3/2007 | Connors, Jr. |
| 2007/0060862 A1 | 3/2007 | Sun et al. |
| 2007/0062856 A1 | 3/2007 | Pahl et al. |
| 2007/0099813 A1 | 5/2007 | Luizzi et al. |
| 2007/0131646 A1 | 6/2007 | Donnelly et al. |
| 2007/0284279 A1 | 12/2007 | Doskoczynski et al. |
| 2008/0017564 A1 | 1/2008 | Hammond |
| 2008/0035484 A1 | 2/2008 | Wu et al. |
| 2008/0035541 A1 | 2/2008 | Franzreb et al. |
| 2008/0045877 A1 | 2/2008 | Levin et al. |
| 2008/0061477 A1 | 3/2008 | Capizzo |
| 2008/0063585 A1 | 3/2008 | Smalley et al. |
| 2008/0081323 A1 | 4/2008 | Keeley et al. |
| 2008/0081362 A1 | 4/2008 | Keeley et al. |
| 2008/0149561 A1 | 6/2008 | Chu et al. |
| 2008/0156648 A1 | 7/2008 | Dudziak et al. |
| 2008/0170982 A1 | 7/2008 | Zhang et al. |
| 2008/0185293 A1 | 8/2008 | Klose et al. |
| 2008/0188836 A1 | 8/2008 | Weber et al. |
| 2008/0190508 A1 | 8/2008 | Booth et al. |
| 2008/0241085 A1 | 10/2008 | Lin et al. |
| 2008/0268016 A1 | 10/2008 | Fang et al. |
| 2008/0290020 A1 | 11/2008 | Marand et al. |
| 2008/0290111 A1 | 11/2008 | Ginsberg et al. |
| 2009/0023572 A1 | 1/2009 | Backes et al. |
| 2009/0032475 A1 | 2/2009 | Ferrer et al. |
| 2009/0039019 A1 | 2/2009 | Raman |
| 2009/0048685 A1 | 2/2009 | Frigstad et al. |
| 2009/0075371 A1 | 3/2009 | Keeley et al. |
| 2009/0078640 A1 | 3/2009 | Chu et al. |
| 2009/0087395 A1 | 4/2009 | Lin et al. |
| 2009/0117335 A1 | 5/2009 | Iyoda et al. |
| 2009/0148495 A1 | 6/2009 | Hammer et al. |
| 2009/0176159 A1 | 7/2009 | Zhamu et al. |
| 2009/0222072 A1 | 9/2009 | Robinson et al. |
| 2009/0236295 A1 | 9/2009 | Braun et al. |
| 2009/0241242 A1 | 10/2009 | Beatty et al. |
| 2009/0283475 A1 | 11/2009 | Hylton et al. |
| 2009/0291270 A1 | 11/2009 | Zettl et al. |
| 2009/0294300 A1 | 12/2009 | Kanzius et al. |
| 2009/0306364 A1 | 12/2009 | Beer et al. |
| 2010/0000754 A1 | 1/2010 | Mann et al. |
| 2010/0016778 A1 | 1/2010 | Chattopadhyay |
| 2010/0021708 A1 | 1/2010 | Kong et al. |
| 2010/0024722 A1 | 2/2010 | Ochs et al. |
| 2010/0024838 A1 | 2/2010 | Ochs et al. |
| 2010/0025330 A1 | 2/2010 | Ratto et al. |
| 2010/0055464 A1 | 3/2010 | Sung |
| 2010/0059378 A1 | 3/2010 | Elson et al. |
| 2010/0072643 A1 | 3/2010 | Pugh et al. |
| 2010/0076553 A1 | 3/2010 | Pugh et al. |
| 2010/0105834 A1 | 4/2010 | Tour et al. |
| 2010/0110372 A1 | 5/2010 | Pugh et al. |
| 2010/0124564 A1 | 5/2010 | Martinson et al. |
| 2010/0127312 A1 | 5/2010 | Grebel et al. |
| 2010/0161014 A1 | 6/2010 | Lynch et al. |
| 2010/0167551 A1 | 7/2010 | Dedontney |
| 2010/0196439 A1 | 8/2010 | Beck et al. |
| 2010/0209330 A1 | 8/2010 | Golzhauser et al. |
| 2010/0209515 A1 | 8/2010 | Chantalat et al. |
| 2010/0213079 A1 | 8/2010 | Willis |
| 2010/0224555 A1 | 9/2010 | Hoek et al. |
| 2010/0228204 A1 | 9/2010 | Beatty et al. |
| 2010/0233781 A1 | 9/2010 | Bangera et al. |
| 2010/0249273 A1 | 9/2010 | Scales et al. |
| 2010/0258111 A1 | 10/2010 | Shah et al. |
| 2010/0323177 A1 | 12/2010 | Ruoff et al. |
| 2010/0327847 A1 | 12/2010 | Leiber et al. |
| 2011/0014217 A1 | 1/2011 | Fahmy et al. |
| 2011/0037033 A1 | 2/2011 | Green et al. |
| 2011/0041519 A1 | 2/2011 | McAlister |
| 2011/0041687 A1 | 2/2011 | Diaz et al. |
| 2011/0045523 A1 | 2/2011 | Strano et al. |
| 2011/0054418 A1 | 3/2011 | Pugh et al. |
| 2011/0054576 A1 | 3/2011 | Robinson et al. |
| 2011/0056892 A1 | 3/2011 | Lancaster |
| 2011/0073563 A1 | 3/2011 | Chang et al. |
| 2011/0092054 A1 | 4/2011 | Seo et al. |
| 2011/0092949 A1 | 4/2011 | Wang |
| 2011/0100921 A1 | 5/2011 | Heinrich |
| 2011/0112484 A1 | 5/2011 | Carter et al. |
| 2011/0118655 A1 | 5/2011 | Fassih et al. |
| 2011/0120970 A1 | 5/2011 | Joo et al. |
| 2011/0124253 A1 | 5/2011 | Shah et al. |
| 2011/0132834 A1 | 6/2011 | Tomioka et al. |
| 2011/0139707 A1 | 6/2011 | Siwy et al. |
| 2011/0152795 A1 | 6/2011 | Aledo et al. |
| 2011/0189440 A1* | 8/2011 | Appleby .............. B22C 9/04 428/156 |
| 2011/0201201 A1 | 8/2011 | Arnold et al. |
| 2011/0202201 A1 | 8/2011 | Matsubara |
| 2011/0253630 A1 | 10/2011 | Bakajin et al. |
| 2011/0258791 A1 | 10/2011 | Batchvarova et al. |
| 2011/0258796 A1 | 10/2011 | Batchvarova et al. |
| 2011/0262645 A1 | 10/2011 | Batchvarova et al. |
| 2011/0263912 A1 | 10/2011 | Miller et al. |
| 2011/0269920 A1 | 11/2011 | Min et al. |
| 2012/0000845 A1 | 1/2012 | Park et al. |
| 2012/0031833 A1 | 2/2012 | Ho et al. |
| 2012/0048804 A1 | 3/2012 | Stetson et al. |
| 2012/0115243 A1 | 5/2012 | Pitkanen et al. |
| 2012/0116228 A1 | 5/2012 | Okubo |
| 2012/0145548 A1 | 6/2012 | Sivan et al. |
| 2012/0148633 A1 | 6/2012 | Sun et al. |
| 2012/0162600 A1 | 6/2012 | Pugh et al. |
| 2012/0183738 A1 | 7/2012 | Zettl et al. |
| 2012/0186850 A1 | 7/2012 | Sugiyama et al. |
| 2012/0211367 A1 | 8/2012 | Vecitis |
| 2012/0218508 A1 | 8/2012 | Pugh et al. |
| 2012/0219203 A1* | 8/2012 | Adachi .............. A61B 6/585 382/132 |
| 2012/0220053 A1 | 8/2012 | Lee et al. |
| 2012/0234453 A1 | 9/2012 | Pugh et al. |
| 2012/0234679 A1 | 9/2012 | Garaj et al. |
| 2012/0235277 A1 | 9/2012 | Pugh et al. |
| 2012/0236254 A1 | 9/2012 | Pugh et al. |
| 2012/0236524 A1 | 9/2012 | Pugh et al. |
| 2012/0241371 A1 | 9/2012 | Revanur et al. |
| 2012/0242953 A1 | 9/2012 | Pugh et al. |
| 2012/0255899 A1 | 10/2012 | Choi et al. |
| 2012/0267337 A1 | 10/2012 | Striemer et al. |
| 2012/0292245 A1 | 11/2012 | Saito |
| 2012/0298396 A1 | 11/2012 | Hong et al. |
| 2012/0301707 A1 | 11/2012 | Kinloch et al. |
| 2013/0015136 A1 | 1/2013 | Bennett |
| 2013/0034760 A1 | 2/2013 | Otts et al. |
| 2013/0045523 A1 | 2/2013 | Leach et al. |
| 2013/0056367 A1 | 3/2013 | Martinez et al. |
| 2013/0071941 A1* | 3/2013 | Miller .............. G01N 23/223 436/145 |
| 2013/0096292 A1 | 4/2013 | Brahmasandra et al. |
| 2013/0100436 A1 | 4/2013 | Jackson et al. |
| 2013/0105417 A1 | 5/2013 | Stetson et al. |
| 2013/0108839 A1 | 5/2013 | Arnold et al. |
| 2013/0116541 A1 | 5/2013 | Gracias et al. |
| 2013/0131214 A1 | 5/2013 | Scales et al. |
| 2013/0135578 A1 | 5/2013 | Pugh et al. |

(56) References Cited

U.S. PATENT DOCUMENTS

| | | |
|---|---|---|
| 2013/0146221 A1 | 6/2013 | Kolmakov et al. |
| 2013/0146480 A1 | 6/2013 | Garaj et al. |
| 2013/0152386 A1 | 6/2013 | Pandojirao-S et al. |
| 2013/0174968 A1 | 7/2013 | Vlassiouk et al. |
| 2013/0174978 A1 | 7/2013 | Pugh et al. |
| 2013/0176030 A1* | 7/2013 | Simon ............. G01V 3/30 |
| | | 324/333 |
| 2013/0190476 A1 | 7/2013 | Lancaster et al. |
| 2013/0192460 A1 | 8/2013 | Miller et al. |
| 2013/0192461 A1 | 8/2013 | Miller et al. |
| 2013/0194540 A1 | 8/2013 | Pugh et al. |
| 2013/0213568 A1 | 8/2013 | Pugh et al. |
| 2013/0215377 A1 | 8/2013 | Pugh et al. |
| 2013/0215378 A1 | 8/2013 | Pugh et al. |
| 2013/0215380 A1 | 8/2013 | Pugh et al. |
| 2013/0216581 A1 | 8/2013 | Fahmy et al. |
| 2013/0240355 A1 | 9/2013 | Ho et al. |
| 2013/0240437 A1 | 9/2013 | Rodrigues et al. |
| 2013/0248097 A1 | 9/2013 | Ploss, Jr. |
| 2013/0248367 A1 | 9/2013 | Stetson et al. |
| 2013/0249147 A1 | 9/2013 | Bedworth |
| 2013/0256118 A1 | 10/2013 | Meller et al. |
| 2013/0256139 A1 | 10/2013 | Peng |
| 2013/0256154 A1 | 10/2013 | Peng |
| 2013/0256210 A1 | 10/2013 | Fleming |
| 2013/0256211 A1 | 10/2013 | Fleming |
| 2013/0261568 A1 | 10/2013 | Martinson et al. |
| 2013/0269819 A1 | 10/2013 | Ruby et al. |
| 2013/0270188 A1 | 10/2013 | Karnik et al. |
| 2013/0273288 A1 | 10/2013 | Luo et al. |
| 2013/0277305 A1 | 10/2013 | Stetson et al. |
| 2013/0277573 A1 | 10/2013 | Miller et al. |
| 2013/0284665 A1 | 10/2013 | Lee et al. |
| 2013/0295150 A1 | 11/2013 | Chantalat et al. |
| 2013/0309776 A1 | 11/2013 | Drndic et al. |
| 2013/0317131 A1 | 11/2013 | Scales et al. |
| 2013/0317132 A1 | 11/2013 | Scales et al. |
| 2013/0317133 A1 | 11/2013 | Scales et al. |
| 2013/0323295 A1 | 12/2013 | Scales et al. |
| 2013/0335092 A1* | 12/2013 | Wu ............. G01V 3/28 |
| | | 324/333 |
| 2013/0338611 A1 | 12/2013 | Pugh et al. |
| 2013/0338744 A1 | 12/2013 | Frewin et al. |
| 2014/0002788 A1 | 1/2014 | Otts et al. |
| 2014/0005514 A1 | 1/2014 | Pugh et al. |
| 2014/0015160 A1* | 1/2014 | Kung ............. H01B 1/04 |
| | | 264/105 |
| 2014/0017322 A1 | 1/2014 | Dai et al. |
| 2014/0030482 A1 | 1/2014 | Miller et al. |
| 2014/0048411 A1 | 2/2014 | Choi et al. |
| 2014/0066958 A1 | 3/2014 | Priewe |
| 2014/0079936 A1 | 3/2014 | Russo et al. |
| 2014/0093728 A1 | 4/2014 | Shah et al. |
| 2014/0128891 A1 | 5/2014 | Astani-Matthies et al. |
| 2014/0141521 A1 | 5/2014 | Peng et al. |
| 2014/0151288 A1 | 6/2014 | Miller et al. |
| 2014/0151631 A1 | 6/2014 | Duesberg et al. |
| 2014/0154464 A1 | 6/2014 | Miller et al. |
| 2014/0170195 A1 | 6/2014 | Fassih et al. |
| 2014/0171541 A1 | 6/2014 | Scales et al. |
| 2014/0174927 A1 | 6/2014 | Bashir et al. |
| 2014/0190004 A1 | 7/2014 | Riall et al. |
| 2014/0190550 A1 | 7/2014 | Loh et al. |
| 2014/0190676 A1 | 7/2014 | Zhamu et al. |
| 2014/0190833 A1 | 7/2014 | Lieber et al. |
| 2014/0192313 A1 | 7/2014 | Riall et al. |
| 2014/0192314 A1 | 7/2014 | Riall et al. |
| 2014/0199777 A2 | 7/2014 | Ruiz et al. |
| 2014/0209539 A1 | 7/2014 | El Badawi et al. |
| 2014/0212596 A1 | 7/2014 | Jahangiri-Famenini |
| 2014/0230653 A1 | 8/2014 | Yu et al. |
| 2014/0230733 A1 | 8/2014 | Miller |
| 2014/0231351 A1 | 8/2014 | Wickramasinghe et al. |
| 2014/0248621 A1 | 9/2014 | Collins |
| 2014/0253131 A1* | 9/2014 | Liu ............. G01V 3/30 |
| | | 324/338 |
| 2014/0257348 A1 | 9/2014 | Priewe et al. |
| 2014/0257515 A1 | 9/2014 | So et al. |
| 2014/0257517 A1 | 9/2014 | Deichmann et al. |
| 2014/0259657 A1 | 9/2014 | Riall et al. |
| 2014/0261999 A1 | 9/2014 | Stetson et al. |
| 2014/0263035 A1 | 9/2014 | Stoltenberg et al. |
| 2014/0263178 A1 | 9/2014 | Sinton et al. |
| 2014/0264977 A1 | 9/2014 | Pugh et al. |
| 2014/0268015 A1 | 9/2014 | Riall et al. |
| 2014/0268020 A1 | 9/2014 | Pugh et al. |
| 2014/0268021 A1 | 9/2014 | Pugh et al. |
| 2014/0268026 A1 | 9/2014 | Pugh et al. |
| 2014/0272286 A1 | 9/2014 | Stoltenberg et al. |
| 2014/0272522 A1 | 9/2014 | Pugh et al. |
| 2014/0273315 A1 | 9/2014 | Pugh et al. |
| 2014/0273316 A1 | 9/2014 | Pugh et al. |
| 2014/0276481 A1 | 9/2014 | Pugh et al. |
| 2014/0276999 A1 | 9/2014 | Harms et al. |
| 2014/0306361 A1 | 10/2014 | Pugh et al. |
| 2014/0308681 A1 | 10/2014 | Strano et al. |
| 2014/0311967 A1 | 10/2014 | Grossman et al. |
| 2014/0315213 A1 | 10/2014 | Nagrath et al. |
| 2014/0318373 A1 | 10/2014 | Wood et al. |
| 2014/0322518 A1 | 10/2014 | Addleman et al. |
| 2014/0333892 A1 | 11/2014 | Pugh et al. |
| 2014/0335661 A1 | 11/2014 | Pugh et al. |
| 2014/0343580 A1 | 11/2014 | Priewe |
| 2014/0346081 A1 | 11/2014 | Sowden et al. |
| 2014/0346631 A1* | 11/2014 | Karim ............. H01L 31/085 |
| | | 257/435 |
| 2014/0349892 A1 | 11/2014 | Van Der Zaag et al. |
| 2014/0350372 A1 | 11/2014 | Pugh et al. |
| 2014/0377651 A1 | 12/2014 | Kwon et al. |
| 2014/0377738 A1 | 12/2014 | Bachmann et al. |
| 2015/0015843 A1 | 1/2015 | Pugh et al. |
| 2015/0017918 A1 | 1/2015 | Pugh et al. |
| 2015/0053627 A1 | 2/2015 | Silin et al. |
| 2015/0057762 A1 | 2/2015 | Harms et al. |
| 2015/0061990 A1 | 3/2015 | Toner et al. |
| 2015/0062533 A1 | 3/2015 | Toner et al. |
| 2015/0063605 A1 | 3/2015 | Pugh |
| 2015/0066063 A1 | 3/2015 | Priewe |
| 2015/0075667 A1 | 3/2015 | McHugh et al. |
| 2015/0077658 A1 | 3/2015 | Pugh et al. |
| 2015/0077659 A1 | 3/2015 | Pugh et al. |
| 2015/0077660 A1 | 3/2015 | Pugh et al. |
| 2015/0077661 A1 | 3/2015 | Pugh et al. |
| 2015/0077662 A1 | 3/2015 | Pugh et al. |
| 2015/0077663 A1 | 3/2015 | Pugh et al. |
| 2015/0077699 A1 | 3/2015 | De Sio et al. |
| 2015/0077702 A9 | 3/2015 | Pugh et al. |
| 2015/0079683 A1 | 3/2015 | Yager et al. |
| 2015/0087249 A1 | 3/2015 | Pugh et al. |
| 2015/0096935 A1 | 4/2015 | Mitra et al. |
| 2015/0098910 A1 | 4/2015 | Mordas et al. |
| 2015/0101931 A1 | 4/2015 | Garaj et al. |
| 2015/0105686 A1 | 4/2015 | Vasan |
| 2015/0118318 A1 | 4/2015 | Fahmy et al. |
| 2015/0122727 A1 | 5/2015 | Karnik et al. |
| 2015/0137817 A1* | 5/2015 | Wilson ............. E21B 43/10 |
| | | 324/333 |
| 2015/0138454 A1 | 5/2015 | Pugh et al. |
| 2015/0142107 A1 | 5/2015 | Pugh et al. |
| 2015/0145155 A1 | 5/2015 | Pugh et al. |
| 2015/0146162 A1 | 5/2015 | Pugh et al. |
| 2015/0147474 A1 | 5/2015 | Batchvarova et al. |
| 2015/0170788 A1 | 6/2015 | Miller et al. |
| 2015/0174253 A1 | 6/2015 | Sun et al. |
| 2015/0174254 A1 | 6/2015 | Sun et al. |
| 2015/0182473 A1 | 7/2015 | Bosnyak et al. |
| 2015/0185180 A1 | 7/2015 | Ruhl et al. |
| 2015/0196579 A1 | 7/2015 | Ferrante et al. |
| 2015/0202351 A1 | 7/2015 | Kaplan et al. |
| 2015/0212339 A1 | 7/2015 | Pugh et al. |
| 2015/0217219 A1 | 8/2015 | Sinsabaugh et al. |
| 2015/0218210 A1 | 8/2015 | Stetson et al. |
| 2015/0221474 A1 | 8/2015 | Bedworth |

(56) References Cited

U.S. PATENT DOCUMENTS

| | | | |
|---|---|---|---|
| 2015/0231557 A1 | 8/2015 | Miller et al. | |
| 2015/0231577 A1 | 8/2015 | Nair et al. | |
| 2015/0247178 A1 | 9/2015 | Mountcastle et al. | |
| 2015/0258254 A1 | 9/2015 | Simon et al. | |
| 2015/0258498 A1 | 9/2015 | Simon et al. | |
| 2015/0258502 A1 | 9/2015 | Turowski | |
| 2015/0258503 A1 | 9/2015 | Sinton et al. | |
| 2015/0258506 A1 | 9/2015 | Mi et al. | |
| 2015/0258525 A1 | 9/2015 | Westman et al. | |
| 2015/0268150 A1 | 9/2015 | Newkirk et al. | |
| 2015/0272834 A1 | 10/2015 | Sun et al. | |
| 2015/0272896 A1 | 10/2015 | Sun et al. | |
| 2015/0273401 A1 | 10/2015 | Miller et al. | |
| 2015/0309337 A1 | 10/2015 | Flitsch et al. | |
| 2015/0321147 A1 | 11/2015 | Fleming et al. | |
| 2015/0321149 A1 | 11/2015 | McGinnis | |
| 2015/0323811 A1 | 11/2015 | Flitsch et al. | |
| 2015/0336202 A1 | 11/2015 | Bedworth et al. | |
| 2015/0342900 A1 | 12/2015 | Putnins | |
| 2015/0346382 A1* | 12/2015 | Bliven | G01T 3/08 250/262 |
| 2015/0351887 A1 | 12/2015 | Peters | |
| 2015/0359742 A1 | 12/2015 | Fassih et al. | |
| 2015/0378176 A1 | 12/2015 | Flitsch et al. | |
| 2016/0009049 A1 | 1/2016 | Stoltenberg et al. | |
| 2016/0038885 A1 | 2/2016 | Hogen-Esch et al. | |
| 2016/0043384 A1 | 2/2016 | Zhamu et al. | |
| 2016/0058932 A1 | 3/2016 | Stetson et al. | |
| 2016/0059190 A1 | 3/2016 | Yoo et al. | |
| 2016/0067390 A1 | 3/2016 | Simon et al. | |
| 2016/0074814 A1 | 3/2016 | Park et al. | |
| 2016/0074815 A1 | 3/2016 | Sinton et al. | |
| 2016/0084008 A1* | 3/2016 | Faircloth | E21B 7/14 175/16 |
| 2016/0084981 A1* | 3/2016 | Kayano | G01V 8/005 324/67 |
| 2016/0116237 A1 | 4/2016 | Alsadah et al. | |
| 2016/0256805 A1 | 9/2016 | Grein et al. | |
| 2016/0272499 A1 | 9/2016 | Zurutuza et al. | |
| 2016/0282326 A1 | 9/2016 | Waduge et al. | |
| 2016/0284811 A1 | 9/2016 | Yu et al. | |
| 2016/0339160 A1 | 11/2016 | Bedworth et al. | |
| 2017/0000937 A1 | 1/2017 | Gottschalk | |
| 2017/0032962 A1 | 2/2017 | Zurutuza et al. | |
| 2017/0035943 A1 | 2/2017 | Simon et al. | |
| 2017/0036916 A1 | 2/2017 | Bedworth et al. | |
| 2017/0037356 A1 | 2/2017 | Simon et al. | |
| 2017/0057812 A1 | 3/2017 | Zurutuza et al. | |
| 2017/0065939 A1 | 3/2017 | Kim et al. | |
| 2017/0144107 A1 | 5/2017 | Garaj et al. | |
| 2017/0202885 A1 | 7/2017 | Agulnick | |
| 2017/0216923 A1 | 8/2017 | Babenko et al. | |
| 2017/0217777 A1 | 8/2017 | Hong et al. | |
| 2017/0239623 A1 | 8/2017 | Stoltenberg et al. | |
| 2017/0296706 A1 | 10/2017 | Simon et al. | |
| 2017/0296972 A1 | 10/2017 | Sinton et al. | |
| 2017/0296976 A1 | 10/2017 | Liu et al. | |
| 2017/0296979 A1 | 10/2017 | Swett et al. | |
| 2018/0147542 A1 | 5/2018 | Jhon et al. | |
| 2018/0207591 A1 | 7/2018 | Yu et al. | |

FOREIGN PATENT DOCUMENTS

| | | |
|---|---|---|
| CN | 1128501 A | 8/1996 |
| CN | 101108194 A | 1/2008 |
| CN | 101243544 | 8/2008 |
| CN | 101428198 A | 5/2009 |
| CN | 101489653 A | 7/2009 |
| CN | 101996853 A | 3/2011 |
| CN | 102242062 A | 11/2011 |
| CN | 102344132 | 2/2012 |
| CN | 102423272 | 4/2012 |
| CN | 102592720 A | 7/2012 |
| CN | 101996853 B | 8/2012 |
| CN | 102637584 A | 8/2012 |
| CN | 103153441 | 6/2013 |
| CN | 103182249 A | 7/2013 |
| CN | 203235358 | 10/2013 |
| CN | 103480281 | 1/2014 |
| CN | 103585891 | 2/2014 |
| CN | 103603706 A | 2/2014 |
| DE | 19536560 | 3/1997 |
| DE | 10 2005 049 388 A1 | 4/2007 |
| EP | 0 364 628 A1 | 4/1990 |
| EP | 1 034 251 | 1/2004 |
| EP | 1 777 250 A1 | 4/2007 |
| EP | 1 872 812 | 1/2008 |
| EP | 2 060 286 | 5/2009 |
| EP | 2 107 120 A1 | 10/2009 |
| EP | 2 230 511 A1 | 9/2010 |
| EP | 1 603 609 | 5/2011 |
| EP | 2 354 272 | 8/2011 |
| EP | 2 450 096 | 5/2012 |
| EP | 2 489 520 | 8/2012 |
| EP | 2 511 002 | 10/2012 |
| EP | 2 586 473 | 5/2013 |
| EP | 2 679 540 | 1/2014 |
| EP | 2 937 313 | 10/2015 |
| EP | 3 070 053 | 9/2016 |
| EP | 3 084 398 | 10/2016 |
| EP | 1 538 2430.5 | 3/2017 |
| EP | 3 135 631 | 3/2017 |
| JP | 59-102111 | 7/1984 |
| JP | 10-510471 | 5/1995 |
| JP | 7504120 | 5/1995 |
| JP | 2001-232158 | 8/2001 |
| JP | 2002-126510 | 5/2002 |
| JP | 2004-179014 | 6/2004 |
| JP | 2005-126966 | 5/2005 |
| JP | 2006-188393 | 7/2006 |
| JP | 2009-291777 | 12/2009 |
| JP | 2011-168448 A | 9/2011 |
| JP | 2011-241479 | 12/2011 |
| JP | 2012-500708 | 1/2012 |
| JP | 2004-202480 | 7/2014 |
| JP | 2015-503405 | 2/2015 |
| JP | 2016-175828 | 10/2016 |
| KR | 102011008411 | 7/2011 |
| KR | 10-2012-0022164 A | 3/2012 |
| KR | 1020120022164 A | 3/2012 |
| KR | 1020140002570 | 1/2014 |
| WO | WO-93/33901 | 3/1993 |
| WO | WO-93/12859 | 8/1993 |
| WO | WO-95/00231 | 1/1995 |
| WO | WO-97/12664 A1 | 4/1997 |
| WO | WO-98/30501 A2 | 7/1998 |
| WO | WO-00/70012 | 11/2000 |
| WO | WO-02/055539 A1 | 7/2002 |
| WO | WO-2013/115762 | 8/2003 |
| WO | WO-2004/009840 A1 | 1/2004 |
| WO | WO-2004/082733 | 9/2004 |
| WO | WO-2005/047857 A2 | 5/2005 |
| WO | WO-2007/103411 A2 | 9/2007 |
| WO | WO-2007/140252 A1 | 12/2007 |
| WO | WO-2008/008533 | 1/2008 |
| WO | WO-2009/129984 A1 | 10/2009 |
| WO | WO-2010/006080 | 1/2010 |
| WO | WO-2010/115904 A1 | 10/2010 |
| WO | WO-2011/019686 A1 | 2/2011 |
| WO | WO-2011/046706 A1 | 4/2011 |
| WO | WO-2011/001674 | 6/2011 |
| WO | WO-2011/063458 A1 | 6/2011 |
| WO | WO-2011/075158 | 6/2011 |
| WO | WO-2011/094204 A2 | 8/2011 |
| WO | WO-2011/100458 A2 | 8/2011 |
| WO | WO-2011/138689 A2 | 11/2011 |
| WO | WO-2012/006657 A1 | 1/2012 |
| WO | WO-2012/021801 A2 | 2/2012 |
| WO | WO-2012/027148 A1 | 3/2012 |
| WO | WO-2012/028695 | 3/2012 |
| WO | WO-2012/030368 A1 | 3/2012 |
| WO | WO-2012/125770 | 9/2012 |
| WO | WO-2012/138671 A2 | 10/2012 |

(56) References Cited

FOREIGN PATENT DOCUMENTS

| WO | WO-2012/142852 A1 | 10/2012 |
|---|---|---|
| WO | WO-2013/016445 A1 | 1/2013 |
| WO | WO-2013/048063 A1 | 4/2013 |
| WO | WO-2013/138137 A1 | 9/2013 |
| WO | WO-2013/138698 A1 | 9/2013 |
| WO | WO-2013/151799 | 10/2013 |
| WO | WO-2013/152179 A1 | 10/2013 |
| WO | WO-2014/084856 | 6/2014 |
| WO | WO-2014/084861 A1 | 6/2014 |
| WO | WO-2014/168629 A1 | 10/2014 |
| WO | WO-2015/030698 A1 | 3/2015 |
| WO | WO-2015/110277 | 7/2015 |
| WO | WO-2015/138736 A1 | 9/2015 |
| WO | WO-2015/138752 A1 | 9/2015 |
| WO | WO-2015/1138771 A1 | 9/2015 |
| WO | WO-2015/197217 | 12/2015 |
| WO | WO-2016/102003 | 6/2016 |

OTHER PUBLICATIONS

Atmeh et al., "Albumin Aggregates: Hydrodynamic Shape and Physico-Chemical Properties," Jordan Journal of Chemistry, 2(2): 169-182 (2007).
Chen et al., "Mechanically Strong, Electrically Conductive, and Biocompatible Graphene Paper," Adv. Mater., 20(18): 3557-3561 (Sep. 2008) (available online Jul. 2008).
CN Office Action in Chinese Application No. 201380013988.9 dated Aug. 18, 2016 (English translation not readily available).
Fuertes, "Carbon composite membranes from Matrimid® and Kapton® polyimides for gas separation," Microporous and Mesoporous Materials, 33: 115-125 (1991).
Galashev, "Computer study of the removal of Cu from the graphene surface using Ar clusters," Computational Materials Science, 98: 123-128 (Feb. 2015) (available online Nov. 2014).
International Search Report and Written Opinion in PCT/US2015/013599 dated Jul. 20, 2015.
International Search Report and Written Opinion in PCT/US2015/013805 dated Apr. 30, 2015.
International Search Report and Written Opinion in PCT/US2015/018114 dated Jun. 3, 2015.
International Search Report and Written Opinion in PCT/US2015/020246 dated Jun. 10, 2015.
International Search Report and Written Opinion in PCT/US2015/020296 dated Jun. 17, 2015.
International Search Report and Written Opinion in PCT/US2015/028948 dated Jul. 16, 2015.
International Search Report and Written Opinion in PCT/US2015/029932 dated Oct. 6, 2015.
Inui et al., "Molecular dynamics simulations of nanopore processing in a graphene sheet by using gas cluster ion beam," Appl. Phys. A, 98: 787-794 (Mar. 2010) (available online Dec. 2009).
Koh et al., "Sensitive NMR Sensors Detect Antibodies to Influenza," NIH PA Author Manuscript PMC (Apr. 2009), also published in Angew. Chem. Int'l. Engl, 47(22): 4119-4121 (May 2008) (available online Apr. 2008).
Lehtinen et al., "Cutting and controlled modification of graphene with ion beams," Nanotechnology, 22: 175306 (8 pages) (Mar. 2011).
Matteucci et al., "Transport of gases and Vapors in Glass and Rubbery Polymers," in Materials Science of Membranes for Gas and Vapor Separation. (Yampolskii et al., eds. 2006) (available online Jun. 2006).
O'Hern et al., "Development of process to transfer large areas of LPCVD graphene from copper foil to a porous support substrate," 1-62 (M.S. Thesis, Massachusetts Institute of Technology, Thesis) (Sep. 2011).
Plant et al. "Size-dependent propagation of Au nanoclusters through few-layer graphene," Nanoscale, 6: 1258-1263 (2014) (available online Oct. 2013).

Popok. "Cluster Ion Implantation in Graphite and Diamond: Radiation Damage and Stopping of Cluster Constituents," Reviews on Advanced Materials Science, 38(1): 7-16 (2014).
Russo et al., "Atom-by-atom nucleation and growth of graphene nanopores," PNAS 109(16): 5953-5957 (Apr. 2012).
U.S. Notice of Allowance in U.S. Appl. No. 14/610,770 dated Aug. 12, 2016.
U.S. Office Action in U.S. Appl. No. 14/656,190 dated Aug. 29, 2016.
U.S. Office Action for U.S. Appl. No. 14/656,580 dated Jun. 2, 2016.
U.S. Office Action in U.S. Appl. No. 14/819,273 dated Jul. 6, 2016.
U.S. Office Action for U.S. Appl. No. 14/856,198 dated Jun. 3, 2016.
Yoon, "Simulations show how to turn graphene's defects into assets," Sciencedaily (Oct. 4, 2016), www.sciencedaily.com/releases/2016/10/161004120428.htm.
Zabihi et al., "Formation of nanopore in a suspended graphene sheet with argon cluster bombardment: A molecular dynamics simulation study," Nuclear Instruments and Methods in Physics Research B, 343: 48-51: (Jan. 2015) (available online Nov. 2014).
Zhang et al. Modern Thin-Film Technology 284-285 (Metallurgical Industry Press, 1st ed. 2009) (English translation not readily available).
Zhao et al. (2012), "Effect of SiO2 substrate on the irradiation-assisted manipulation of supported graphene: a molecular dynamics study," Nanotechnology 23(28): 285703 (Jul. 2012) (available online Jun. 2012).
Zhao et al. (May 2012), "Drilling Nanopores in Graphene with Clusters: A Molecular Dynamics Study," J. Phys. Chem. C, 116(21): 11776-11178 (2012) (available online May 2012).
Chen et al., "Hierarchically porous graphene-based hybrid electrodes with excellent electrochemical performance", Journal of Materials Chemistry A: Materials for Energy and Sustainability, vol. 1, No. 33, Jan. 1, 2003, pp. 9409-9413.
Chinese Office Action in Application No. 201580006829.5 dated Jan. 23, 2018 (with English translation) (13 pages).
European Extended Search Report in Application No. 15786691.4 dated Dec. 1, 2017 (10 pages).
European Extended Search Report in Application No. 15789852.9 dated Dec. 6, 2017 (8 pages).
Japanese Office Action in Application No. 2017-042023 dated Jan. 9, 2018 (with English translation) (9 pages).
Singapore Search Report and Written Opinion in Application No. 11201701654U dated Dec. 6, 2017 (6 pages).
Taiwanese Office Action in Application No. 102146079 dated Dec. 12, 2017 (with English translation) (4 pages).
U.S. Notice of Allowance in U.S. Appl. No. 14/843,944 dated Feb. 9, 2018 (9 pages).
U.S. Office Action for U.S. Appl. No. 15/099,482 dated Feb. 23, 2018 (9 pages).
U.S. Office Action in U.S. Appl. No. 14/609,325 dated Jan. 16, 2018 (11 pages).
U.S. Office Action in U.S. Appl. No. 14/656,190 dated Jan. 10, 2018 (14 pages).
U.S. Office Action in U.S. Appl. No. 14/856,471 dated Jan. 11, 2018 (36 pages).
U.S. Office Action in U.S. Appl. No. 15/099,099 dated Feb. 15, 2018 (13 pages).
U.S. Office Action in U.S. Appl. No. 15/099,588 dated Feb. 1, 2018 (6 pages).
Wang et al., "Preparation of high-surface-area carbon nanoparticle/graphene composites", Carbon, Elsevier, Oxford, GB, vol. 50, No. 10, Apr. 8, 2012, pp. 3845-3853.
Office Action for Indian Appl. Ser. No. 1566/DELNP/2013 dated Feb. 2, 2018 (7 pages).
Office Action for Japanese Appl. Ser. No. 2016-521448 dated Mar. 16, 2018 (5 pages).
Skrzypek et al., "Pancreatic islet macroencapsulation using microwell porous membranes", Scientific Reports, 7: 9186 | DOI:10.1038/s41598-017-09647-7, Aug. 23, 2017 (12 pages).
U.S. Notice of Allowance for U.S. Appl. No. 15/099,464 dated Feb. 28, 2018 (5 pages).

(56) References Cited

OTHER PUBLICATIONS

U.S. Office Action for U.S. Appl. No. 15/099,276 dated Mar. 22, 2018 (13 pages).
U.S. Office Action for U.S. Appl. No. 15/453,441 dated Mar. 22, 2018 (7 pages).
Adiga et al., "Nanoporous Materials for Biomedical Devices," JOM 60: 26-32 (Mar. 25, 2008).
AMI Applied Membranes Inc. (undated). FilmTec Nanofiltration Membrane Elements. Retrieved Jun. 1, 2016, from http://www.appliedmembranes.com/filmtec-nanofiltration-membrane-elements.html.
Apel, "Track etching technique in membrane technology," Radiation Measurements 34(1-6): 559-566 (Jun. 2001).
Bae et al., "Roll-to-roll production of 30-inch graphene films for transparent electrodes," Nature Nanotechnology 5: 574-578 (Jun. 20, 2010).
Bai et al., "Graphene nanomesh," Nature Nanotechnology 5: 190-194 (Feb. 14, 2010).
Baker. (2004). Track-etch Membranes. In Membrane Technology and Applications (2nd ed., pp. 92-94). West Sussex, England: John Wiley & Sons.
Butler et al. "Progress, Challenges, and Opportunities in Two-Dimensional Materials Beyond Graphene", Materials Review 7(4): 2898-2926 (Mar. 6, 2013).
Chhowalla et al., "The chemistry of two-dimensional layered transition metal dichalcogenide nanosheets," Nature Chemistry 5: 263-275 (Mar. 20, 2013).
Childres et al., "Effect of oxygen plasma etching on graphene studied using Raman spectroscopy and electronic transport measurements," New Journal of Physics 13 (Feb. 10, 2011).
Clochard. (undated). Radiografted track-etched polymer membranes for research and application [Scholarly project]. In Laboratoire Des Solides Irradiés. Retrieved Jun. 2, 2016, from http://iramis.cea.fr/radiolyse/5juin2015/Clochard.pdf.
Cohen-Tanugi et al, "Water Desalination across Nanoporous Graphene," ACS Nano Letters 12(7): 3602-3608 (Jun. 5, 2012).
Cohen-Tanugi, "Nanoporous graphene as a water desalination membrane," Thesis: Ph.D., Massachusetts Institute of Technology, Department of Materials Science and Engineering (Jun. 2015).
Colton, "Implantable biohybrid artificial organs," Cell Transplantation 4(4): 415-436 (Jul.-Aug. 1995).
Desai et al., "Nanoporous microsystems for islet cell replacement," Advanced Drug Delivery Reviews 56: 1661-1673 (Jul. 23, 2004).
Fischbein et al., "Electron beam nanosculpting of suspended graphene sheets," Applied Physics Letters 93(113107): 1-3, (Sep. 16, 2008).
Fissell et al., "High-Performance Silicon Nanopore Hemofiltration Membranes," NIH-PA Author Manuscript, PMC, (Jan. 5, 2010), also published in J. Memb. Sci. 326(1): 58-63 (Jan. 5, 2009).
Gimi et al., "A Nanoporous, Transparent Microcontainer for Encapsulated Islet Therapy," J. Diabetes Sci. Tech. 3(2): 1-7 (Mar. 2009).
Jiang et al., "Porous Graphene as the Ultimate Membrane for Gas Separation," Nano Letters 9(12): 4019-4024 (Sep. 23, 2009).
Joshi et al., "Precise and ultrafast molecular sieving through graphene oxide membranes", Science 343(6172): 752-754 (Feb. 14, 2014).
Kanani et al., "Permeability—Selectivity Analysis for Ultrafiltration: Effect of Pore Geometry," NIH-PA Author Manuscript, PMC, (Mar. 1, 2011), also published in J. Memb. Sci. 349(1-2): 405 (Mar. 1, 2010).
Karan et al., "Ultrafast Viscous Permeation of Organic Solvents Through Diamond-Like Carbon Nanosheets," Science 335: 444-447 (Jan. 27, 2012).
Kim et al., "Fabrication and Characterization of Large Area, Semiconducting Nanoperforated Graphene Materials," Nano Letters 10(4): 1125-1131 (Mar. 1, 2010).
Kim et al., "The structural and electrical evolution of graphene by oxygen plasma-induced disorder," Nanotechnology IOP 20(375703): 1-8 (Aug. 26, 2009).
Koski and Cui, "The New Skinny in Two-Dimensional Nanomaterials", ACS Nano 7(5): 3739-3743 (May 16, 2013).
Liu et al., "Atomically Thin Molybdenum Disulfide Nanopores with High Sensitivity for DNA Translocation," ACS Nano 8(3): 2504-2511 (Feb. 18, 2014).
Liu et al., "Graphene Oxidation: Thickness-Dependent Etching and Strong Chemical Doping," Nano Letters 8(7): 1965-1970 (Jun. 19, 2008).
Mishra et al., "Functionalized Graphene Sheets for Arsenic Removal and Desalination of Sea Water," Desalination 282: 39-45 (Nov. 1, 2011).
Morse, "Scalable Synthesis of Semiconducting Nanopatterned Graphene Materials," InterNano Resources for Nanomanufacturing (undated). Retrieved Jun. 2, 2016 from: http://www.internano.org/node/345.
Nair et al., "Unimpeded Permeation of Water Through Helium-Leak-tight Graphene-Based Membranes," Science 335: 442-444 (Jan. 27, 2012).
O'Hern et al. "Selective Molecular Transport through Intrinsic Defects in a Single Layer of CVD Graphene," ACS Nano, 6(11): 10130-10138 (Oct. 2, 2012).
O'Hern et al., "Selective Ionic Transport through Tunable Subnanometer Pores in Single-Layer Graphene Membranes," Nano Letters 14(3): 1234-1241 (Feb. 3, 2014).
Paul, "Creating New Types of Carbon-Based Membranes," Science 335: 413-414 (Jan. 27, 2012).
Schweicher et al., "Membranes to achieve immunoprotection of transplanted islets," NIH-PA Author Manuscript, PMC, (Nov. 13, 2014), also published in Frontiers in Bioscience (Landmark Ed) 19: 49-76 (Jan. 1, 2014).
Sint et al., "Selective Ion Passage through Functionalized Graphene Nanopores," JACS 130: 16448-16449 (Nov. 14, 2008).
Suk et al., "Water Transport Through Ultrathin Graphene," Journal of Physical Chemistry Letters 1(10): 1590-1594 (Apr. 30, 2010).
Tan et al., "Beta-cell regeneration and differentiation: how close are we to the 'holy grail'?" J. Mol. Encodrinol. 53(3): R119-R129 (Dec. 1, 2014).
Vlassiouk et al., "Versatile ultrathin nanoporous silicon nitride membranes," Proc. Natl. Acad. Sci. USA 106(50): 21039-21044 (Dec. 15, 2009).
Wadvalla, "Boosting agriculture through seawater," Nature Middle East (Jul. 2, 2012). Retrieved Jun. 1, 2016 from: natureasia.com/en/nmiddleeast/article/10.1038/nmiddleeast.2012.92?WT.mc_id=FBK NatureMEast].
Wikipedia, "Ion track." Jun. 1, 2016. Retrieved Jun. 1, 2016 from: en.wikipedia.org/wiki/ion_track.
Xu et al., "Graphene-like Two-Dimensional Materials", Chemical Reviews 113: 3766-3798 (Jan. 3, 2013).
Zan et al., "Graphene Reknits Its Holes," Nano Lett. 12(8): 3936-3940 (Jul. 5, 2012).
Zhao et al. "Two-Dimensional Material Membranes: An Emerging Platform for Controllable Mass Transport Applications," Small 10(22): 4521-4542 (Sep. 10, 2014).
AE Search and Examination Report for United Arab Emirates Application No. P186/13 dated Oct. 4, 2016.
Agenor et al., "Renal tubular dysfunction in human visceral leishmaniasis (Kala-azar)," Clinical Nephrology 71(5): 492-500 (May 2009) (available online Mar. 21, 2011).
Albert et al., "Ringer's lactate is compatible with the rapid infusion of AS-3 preserved packed red blood cells," Can. J. Anaesth. 56(5): 352-356 (May 2009) (available online Apr. 2, 2009).
Aluru et al. "Modeling electronics on the nanoscale." Handbook of nanoscience, engineering and technology Goddard W, Brenner D, Lyshevski S, Iafrate GJ (2002): 11-1.
Alvarenga, "Carbon nanotube materials for aerospace wiring" Rochester Institute of Technology, 2010.
AMI Applied Membranes Inc., "Filmtec Nanofiltration Membrane Elements", Retrieved from appliedmembranes.com/nanofiltration_elements.htm, accessed Apr. 28, 2015 (2 Pages).
Aso et al., "Comparison of serum high-molecular weight (HMW) adiponectin with total adiponectin concentrations in type 2 diabetic patients with coronary artery using a novel enzyme-linked immunosorbent assay to detect HMW adiponectin," Diabetes 55(7): 1954-1960 (Jul. 2006).
AU Examination Report for Australian Patent Application No. 2013235234, dated Jan. 13, 2017, 4 pages.

(56) References Cited

OTHER PUBLICATIONS

AU Examination Report for Australian Patent Application No. 2013363283, dated Jun. 20, 2017, 4 pages.
AU Notice of Acceptance for Australian Application No. 2011293742 dated Jan. 13, 2016.
Axelsson et al., "Acute hyperglycemia induces rapid, reversible increases in glomerular permeability in nondiabetic rats," Am. J. Physiol. Renal Physiol. 298(6): F1306-F1312 (Jun. 2010) (available online Mar. 17, 2010).
Bains et al., "Novel lectins from rhizomes of two Acorus species with mitogenic activity and inhibitory potential towards murine cancer cell lines," Int'l Immunopharmacol. 5(9): 1470-1478 (Aug. 2005) (available online May 12, 2005).
Baker, "Membrane Technology and Applications", Membrane Technology and Applications; Apr. 14, 2004; pp. 92-94.
Barreiro et al. "Transport properties of graphene in the high-current limit." Physical review letters 103.7 (2009): 076601.
Bazargani et al. "Low molecular weight heparin improves peritoneal ultrafiltration and blocks complement and coagulation," Peritoneal Dialysis Int'l 25(4): 394-404 (Jul. 2005-Aug. 2005).
Bazargani, "Acute inflammation in peritoneal dialysis: experimental studies in rats. Characterization of regulatory mechanisms," Swedish Dental J. Supp. 171: 1-57, i (2005).
Beppu et al., "Antidiabetic effects of dietary administration of Aloe arborescens Miller components on multiple low-dose streptozotocin-induced diabetes in mice: investigation on hypoglycemic action and systemic absorption dynamics of aloe components," J. Ethnopharmacol. 103(3): 468-77 (Feb. 20, 2006) (available online Jan. 6, 2006).
Bieri et al. "Two-dimensional Polymer Formation on Surfaces: Insight into the Roles of Precursor Mobility and Reactivity" JACS, 2010, vol. 132, pp. 16669-16676.
Bruin et al., "Maturation and function of human embryonic stem cell-derived pancreatic progenitors in macroencapsulation devices following transplant into mice", Diabetologia (2013), vol. 56: 1987-1998 (Jun. 16, 2013).
Chu Ju, et al. "Modern Biotechnology" East China University of Technology Press, (Sep. 2007), vol. 1; pp. 306-307, ISBN 978-7-5628-2116-8.
Clochard, "Track-Etched Polymer Membranes," Laboratory of Irradiated Solids, Ecole Polytechnique, retrieved from http://www.lsi.polytechnique.fr/home/research/physics-and-chemistry-of-nanoobjects/trac . . . , Accessed Jul. 30, 2015 (2 pages).
CN Notification of Grant for Chinese Application No. 201180049184.5 dated Jun. 6, 2016.
CN Office Action for Chinese Application No. 201380014845.X dated Jul. 8, 2016.
CN Office Action for Chinese Application No. 201380014845.X dated Sep. 2, 2015.
CN Office Action for Chinese Application No. 201380019165.5 dated Aug. 25, 2015.
CN Office Action for Chinese Application No. 201380073141.X dated Jun. 8, 2016.
CN Office Action for Chinese Application No. 201380073141.X dated Mar. 21, 2017.
CN Office Action for Chinese Application No. 201480015372.X dated Aug. 2, 2016.
CN Office Action for Chinese Application No. 20118004918.5 dated Jun. 15, 2015.
CN Office Action for Chinese Application No. 201180049184.5 dated Jul. 30, 2014.
CN Office Action for Chinese Application No. 201180049184.5 dated Mar. 4, 2016.
CN Office Action for Chinese Application No. 201380014845.X dated Dec. 23, 2016.
CN Office Action for Chinese Application No. 201380017644.5 dated Feb. 7, 2017.
CN Office Action for Chinese Application No. 201380017644.5 dated May 26, 2016.
CN Office Action for Chinese Application No. 201380017644.5 dated Sep. 29, 2015.
CN Office Action in Chinese Application No. 201380013988.9 dated Oct. 27, 2015.
Daniel et al. "Implantable Diagnostic Device for Cancer Monitoring." Biosens Bioelectricon. 24(11): 3252-3257 (Jul. 15, 2009).
Database WPI, Week 201238, Thomson Scientific, London, GB; AN 2012-D49442.
De Lannoy et al., "Aquatic Biofouling Prevention by Electrically Charged Nanocomposite Polymer Thin Film Membranes", 2013 American Water Work Association membrane Technology Conference; Environmental science & technology 47.6 (2013): 2760-2768.
Deng et al., "Renal protection in chronic kidney disease: hypoxia-inducible factor activation vs. angiotensin II blockade," Am. J. Physiol. Renal Physiol. 299(6): F1365-F1373 (Dec. 2010) (available online Sep. 29, 2010).
Edwards, "Large Sheets of Graphene Film Produced for Transparent Electrodes (w/ Video)"; (Jun. 21, 2010), PhysOrg.com, retrieved on May 15, 2017 from https://phys.org/news/2010-06-large-sheets-graphene-transparentelectrodes.html (2 pages).
EP Office Action for European Application No. 13715529.7 dated Jun. 24, 2016.
Fayerman, "Canadian scientists use stem cells to reverse diabetes in mice", The Telegraph-Journal (New Brunswick), 1-2 (Jun. 29, 2012).
Fayerman, "Diabetes reversed in mice; University of B.C. scientists use embryonic stem cells to deal with Type 1 disease", The Vancouver Sun (British Columbia), 1-2 (Jun. 28, 2012).
Fejes et al. "A review of the properties and CVD synthesis of coiled carbon nanotubes." Materials 3.4 (2010): 2618-2642.
Franzen, C. "MIT Setting Up Industrial-Scale Graphene Printing Press" Sep. 23, 2011, retrieved from http://talkingpointsmemo.com/idealab/mit-setting-up-industrial-scale-graphene-printing-press (2 pages).
Freedman et al., "Genetic basis of nondiabetic end-stage renal disease," Semin. Nephrol. 30(2): 101-110 (Mar. 2010).
Garcia-Lopez et al., "Determination of high and low molecular weight molecules of icodextrin in plasma and dialysate, using gel filtration chromatography, in peritoneal dialysis patients," Peritoneal Dialysis Int'l 25(2): 181-191 (Mar. 2005-Apr. 2005).
Georgakilas et al., "Functionalization of Graphene: Covalent and Non-Covalent Approaches, Derivatives and Applications," Chem. Rev., (2012) 112(11), pp. 6156-6214.
Gnudi "Molecular mechanisms of proteinuria in diabetes," Biochem. Soc. Trans. 36(5): 946-949 (Oct. 2008).
Gotloib et al., "Peritoneal dialysis in refractory end-stage congestive heart failure: a challenge facing a no-win situation," Nephrol. Dialysis. Transplant. 20(Supp. 7): vii32-vii36 (Jul. 2005).
Harvey "Carbon as conductor: a pragmatic view." Proceedings of the 61st IWCS Conference, http://www. iwcs. org/archives/56333-iwcs-2012b-1.1584632. vol. 1. 2012.
Hashimoto et al. "Direct evidence for atomic defects in graphene layers." Nature 430.7002 (2004): 870-873.
He, et al. "The attachment of Fe3 04 nanoparticles to graphene oxide by covalent bonding." Carbon 48.11 (2010): 3139-3144.
Hone et al. "Graphene has record-breaking strength" Physicsworld.com, Jul. 17, 2008.
Huang et al., "Gene expression profile in circulating mononuclear cells afterexposure to ultrafine carbon particles," Inhalation Toxicol. 22(10): 835-846 (Aug. 2010).
Humplik, et al. "Nanostructured materials for water desalination." Nanotechnology 22.29 (2011): 292001.
International Search Report and Written Opinion dated Jan. 5, 2012 for related International Application No. PCT/US11/47800.
International Search Report and Written Opinion dated Jul. 5, 2017 from related PCT application PCT/US2017/024147.
International Search Report and Written Opinion dated Mar. 12, 2014 for International Application No. PCT/US2013/074942.
International Search Report and Written Opinion for International Application No. PCT/US2011/047800 dated Jan. 5, 2012.
International Search Report and Written Opinion for PCT Application No. PCT/US2014/023027 dated Jun. 26, 2014.
International Search Report and Written Opinion in International Application No. PCT/US2013/030344 dated Jun. 19, 2013.
International Search Report and Written Opinion in International Application No. PCT/US2013/033035 dated Jun. 28, 2013.

(56) References Cited

OTHER PUBLICATIONS

International Search Report and Written Opinion in International Application No. PCT/US2013/033400, dated Jun. 28, 2013.
International Search Report and Written Opinion in International Application No. PCT/US2013/033403 dated Jun. 28, 2013.
International Search Report and Written Opinion in PCT/US2014/041766, dated Sep. 30, 2014.
International Search Report and Written Opinion dated Jun. 5, 2014 in International Application No. PCT/US2014/021677.
International Search Report and Written Opinion dated Jun. 6, 2014 in International Application No. PCT/US2014/023043.
International Search Report and Written Opinion dated Dec. 16, 2014, for International Application No. PCT/US2014/051011.
International Search Report and Written Opinion dated Jun. 19, 2015, in International Application No. PCT/US2015/020287.
Inui et al. "Molecular dynamics simulations of nanopore processing in a graphene sheet by using gas cluster ion beam." Applied Physics A: Materials Science & Processing 98.4 (2010): 787-794.
Israelachvili, "Intermolecular and Surface Forces," 3rd ed., Chap. 7.1, Sizes of Atoms, Molecules, and Ions, 2011, 1 page.
Jiao et al., "Castration differentially alters basal and leucine-stimulated tissue protein synthesis in skeletal muscle and adipose tissue," Am. J. Physiol. Endocrinol. Metab. 297(5): E1222-1232 (Nov. 2009) (available online Sep. 15, 2009).
JP Office Action in Japanese Application No. 2015-501729 dated Dec. 9, 2016 (English translation).
JP Office Action in Japanese Application No. 2015-501729 dated Jun. 20, 2017 (English translation).
JP Office Action in Japanese Application No. 2015-501867 dated Oct. 11, 2016 (English translation).
JP Office Action in Japanese Application No. 2015-503405 dated Nov. 14, 2016 (English translation).
JP Office Action in Japanese Application No. 2015-503406 dated Dec. 6, 2016(English translation).
Kang et al., "Effect of eplerenone, enalapril and their combination treatment on diabetic nephropathy in type II diabetic rats," Nephrol. Dialysis Transplant. 24(1): 73-84 (Jan. 2009).
Kang et al., "Efficient Transfer of Large-Area Graphene Films onto Rigid Substrates by Hot Pressing," American Chemical Society Nano, 6(6): 5360-5365(May 28, 2012).
Kar et al., "Effect of glycation of hemoglobin on its interaction with trifluoperazine," Protein J. 25(3): 202-211 (Apr. 2006) (available online Jun. 6, 2006).
Kawamoto et al., "Serum high molecular weight adiponectin is associated with mild renal dysfunction in Japanese adults," J. Atherosclerosis Thrombosis 17(11): 1141-1148 (Nov. 27, 2011).
Khun et al. "From Microporous Regular Frameworks to Mesoporous Materials with Ultrahigh Surface Area: Dynamic reorganization of Porous Polvmer Networks" JACS, 2008; vol. 130; pp. 13333-13337.
Krupka et al., "Measurements of the Sheet Resistance and Conductivity of Thin Epitaxial Graphene and SiC Films" Applied Physics Letters 96, 082101-I; Feb. 23, 2010.
Kumar et al., "Modulation of alpha-crystallin chaperone activity in diabetic rat lens by curcumin," Molecular Vision 11: 561-568 (Jul. 26, 2005).
Lathuiliere et al., "Encapsulated Cellular Implants for Recombinant Protein Delivery and Therapeutic Modulation of the Immune System," Journal of Applied Physics, Int. J. Mol. Sci., 16: 10578-10600 (May 8, 2015).
Lee, et al. "Measurement of the elastic properties and intrinsic strength of monolayer graphene." science 321.5887 (2008): 385-388.
Lucchese et al. "Quantifying ion-induced defects and Raman relaxation length in graphene." Carbon 48.5 (2010): 1592-1597.
Macleod et al. "Supramolecular Orderinng in Oligothiophene-Fullerene Monolayers" JACS, 2009, vol. 131, pp. 16844-16850.
Mattevi et al. "A review of chemical vapour deposition of graphene on copper." Journal of Materials Chemistry 21.10 (2011): 3324-3334.

Miao et al. "Chemical vapor deposition of grapheme" INTECH Open Access Publisher, 2011.
MIT/MTL Center for Graphene Devices and 2D Systems, retrieved from: http://www-mtl.mit.edu/wpmu/graphene/ [retrieved from Aug. 21, 2014 archive] (3 pages).
MIT/MTL Center for Graphene Devices and 2D Systems, retrieved from: http://www-mtl.mit.edu/wpmu/graphene/ [retrieved from Mar. 4, 2015 archive] (3 pages).
Nafea, et al. "Immunoisolating semi-permeable membranes for cell encapsulation: focus on hydrogels." J Control Release. 154(2): 110-122 (Sep. 5, 2011).
Nezlin, "Circulating non-immune IgG complexes in health and disease," Immunol. Lett. 122(2); 141-144 (Feb. 21, 2009) (available online Feb. 2, 2009).
Norata et al., "Plasma adiponectin levels in chronic kidney disease patients: relation with molecular inflammatory profile and metabolic status," Nutr. Metab. Cardiovasc. Dis. 20(1): 56-63 (Jan. 2010) (available online Apr. 9, 2009).
Ogawa et al., "Exosome-like vesicles in Gloydius blomhoffii blomhoffii venom," Toxicon 51(6): 984-993 (May 2008) (available online Feb. 19, 2008).
Ohgawara et al. "Assessment of pore size of semipermeable membrane for immunoisolation on xenoimplatntation of pancreatic B cells using a diffusion chamber." Transplant Proc. (6): 3319-3320. 1995.
Oki et al., "Combined acromegaly and subclinical Cushing disease related to high-molecular-weight adrenocorticotropic hormone," J. Neurosurg. 110(2): 369-73 (Feb. 2009).
Osorio et al., "Effect of treatment with losartan on salt sensitivity and SGLT2 expression in hypertensive diabetic rats," Diabetes Res. Clin. Pract. 86(3): e46-e49 (Dec. 2009) (available online Oct. 2, 2009).
Osorio et al., "Effect of phlorizin on SGLT2 expression in the kidney of diabetic rats," J. Nephrol. 23(5): 541-546 (Sep.-Oct. 2010).
Padidela et al., "Elevated basal and post-feed glucagon-like peptide 1 (GLP-1) concentrations in the neonatal period," Eur. J. Endocrinol. 160(1): 53-58 (Jan. 2009) (available online Oct. 24, 2008).
Pall Corporation, "Pall Water Processing Disc-Tube Filter Technology", Retrieved on Feb. 10, 2015, Retrieved from http://www.pall.com /pdfs/Fuels-and-Chemicals/Disc-Tube_Filter_Technology-DT100b.pdF (15 Pages).
Plant et al. "Size-dependent propagation of Au nanoclusters through few-layer grapheme," The Royal Society of Chemistry 2013, Nanoscale.
Pollard, "Growing Graphene via Chemical Vapor" Department of Physics, Pomona College; May 2, 2011.
Rafael et al. "Cell Transplantation and Immunoisolation: Studies on a macroencapsultaion device." From the Departments of Transplantation Pathology: Stockholm, Sweden (1999).
Rezania et al., "Enrichment of Human Embryonic Stem Cell-Derived NKX6.1-Expressing Pancreatic Progenitor Cells Accelerates the Maturation of Insulin-Secreting Cells In Vivo", Stem Cells Regenerative Medicine, vol. 31: 2432-2442 (Jul. 29, 2013).
Rezania et al., "Maturation of Human Embryonic Stem Cell-Derived Pancreatic Progenitors Into Functional Islets Capable of Treating Pre-existing Diabetes in Mice", Diabetes Journal, vol. 61: 2016-2029 (Aug. 1, 2012).
Ribeiro et al., "Binary Mutual Diffusion Coefficients of Aqueous Solutions of Sucrose, Lactose, Glucose, and Fructose in the Temperature Range from (298.15 to 328.15) K," J. Chem. Eng. Data 51(5): 1836-1840 (Sep. 2006) (available online Jul. 20, 2006).
Rippe et al., "Size and charge selectivity of the glomerular filter in early experimental diabetes in rats," Am. J. Physiol. Renal Physiol. 293(5): F1533-F1538 (Nov. 2007)(available online Aug. 15, 2007).
SA Final Rejection for Saudi Arabia Application No. 113340400 dated Jan. 28, 2016.
SA First Examination Report for Saudi Arabia Application No. 113340401 dated Apr. 28, 2015.
SA First Examination Report for Saudi Arabia Application No. 113340424 dated May 10, 2015.
SA First Examination Report for Saudi Arabia Application No. 113340426 dated May 12, 2015.

(56) References Cited

OTHER PUBLICATIONS

SA First Examination Report in Saudi Arabia Application No. 113340400 dated Apr. 13, 2015.
SA Second Examination Report for Saudi Arabia Application No. 113340400 dated Aug. 11, 2015.
Sanchez, et al. "Biological Interactions of Graphene-Family Nanomaterials—An Interdisciplinary Review." Chem Res Toxicol. 25(1): 15-34 (Jan. 13, 2012).
Sethna et al., "Serum adiponectin levels and ambulatory blood pressure monitoring in pediatric renal transplant recipients," Transplantation 88(8): 1030-1037 (Oct. 27, 2009).
Sullivan et al., "Microarray analysis reveals novel gene expression changes associated with erectile dysfunction in diabetic rats," Physiol. Genom. 23(2): 192-205 (Oct. 17, 2005) (available online Aug. 23, 2005).
Swett et al, "Imagining and Sculpting Graphene on the atomic scale" Oak Ridge National Laboratory's (ORNL) Center for Nanophase Materials Sciences (CNMS) Biannual Review. 1 page.
Swett et al, "Supersonic Nanoparticle Interaction with Suspended CVD Graphene", Microsc. Microanal. 22 (Suppl 3): 1670-1671 (Jul. 25, 2016).
Takata et al., "Hyperresistinemia is associated with coexistence of hypertension and type 2 diabetes," Hypertension 51. 2 (Feb. 2008): 534-9.
Tamborlane et al., "Continuous Glucose Monitoring and Intensive Treatment of Type 1 Diabetes" N Engl J Med 359;14: 1464-1476 (Oct. 2, 2008).
Tanugi et al., "Nanoporous Graphene Could Outperform Best Commercial Water Desalination Techniques,"; ACS 2012; Jun. 25, 2012; Weftec 2012; Sep. 29-Oct. 3.
Totani et al. "Gluten binds cytotoxic compounds generated in heated frying oil." Journal of oleo science 57.12 (2008): 683-690.
Tsukamoto et al. "Purification, characterization and biological activities of a garlic oliqosaccharide," Journal of UOEH 30.2 (Jun. 1, 2008): 147-57.
TW Office Action in Taiwanese Application No. 102146079 dated Apr. 14, 2017. 9 Pages.(English translation).
TW Search Report in Taiwanese Application No. 102146079 dated Apr. 14, 2017. 1 page.
UMEA Universitet "Graphene nanoscrolls are formed by decoration of magnetic nanoparticles." ScienceDaily. Aug. 15, 2013. https://www.sciencedaily.com/releases/2013/08/130815084402.htm (3 pages).
U.S. Notice of Allowance for U.S. Appl. No. 12/868,150 dated Sep. 25, 2012.
U.S. Notice of Allowance for U.S. Appl. No. 13/548,539 dated Aug. 18, 2015.
U.S. Notice of Allowance for U.S. Appl. No. 13/548,539 dated Jul. 23, 2015.
U.S. Notice of Allowance for U.S. Appl. No. 13/719,579 dated May 20, 2016.
U.S. Notice of Allowance for U.S. Appl. No. 13/795,276 dated Oct. 7, 2016.
U.S. Notice of Allowance for U.S. Appl. No. 13/802,896 dated Apr. 1, 2015.
U.S. Notice of Allowance for U.S. Appl. No. 13/803,958 dated Aug. 29, 2016.
U.S. Notice of Allowance for U.S. Appl. No. 13/803,958 dated Jun. 2, 2016.
U.S. Notice of Allowance for U.S. Appl. No. 13/803,958 dated Sep. 12, 2016.
U.S. Notice of Allowance for U.S. Appl. No. 13/804,085 dated Jan. 15, 2015.
U.S. Notice of Allowance for U.S. Appl. No. 13/804,085 dated Mar. 12, 2015.
U.S. Notice of Allowance for U.S. Appl. No. 13/923,503 dated Oct. 14, 2016.
U.S. Notice of Allowance for U.S. Appl. No. 13/923,503 dated Oct. 5, 2016.
U.S. Notice of Allowance for U.S. Appl. No. 14/200,195 dated Jul. 5, 2016.
U.S. Notice of Allowance for U.S. Appl. No. 14/200,530 dated Aug. 1, 2016.
U.S. Notice of Allowance for U.S. Appl. No. 14/203,655 dated Dec. 9, 2016.
U.S. Notice of Allowance in U.S. Appl. No. 12/868,150 dated Sep. 25, 2012.
U.S. Notice of Allowance in U.S. Appl. No. 13/795,276 dated Jan. 19, 2017.
U.S. Notice of Allowance in U.S. Appl. No. 13/803,958 dated Aug. 29, 2016.
U.S. Notice of Allowance in U.S. Appl. No. 13/803,958 dated Sep. 12, 2016.
U.S. Notice of Allowance in U.S. Appl. No. 14/610,770 dated May 5, 2017.
U.S. Notice of Allowance in U.S. Appl. No. 14/656,580 dated May 8, 2017.
U.S. Notice of Allowance in U.S. Appl. No. 14/819,273 dated Jun. 9, 2017.
U.S. Notice of Allowance in U.S. Appl. No. 15/099,464 dated Jun. 16, 2017.
U.S. Office Action for U.S. Appl. No. 13/548,539 dated Feb. 6, 2015.
U.S. Office Action for U.S. Appl. No. 13/719,579 dated Jul. 8, 2015.
U.S. Office Action for U.S. Appl. No. 13/719,579 dated May 4, 2016.
U.S. Office Action for U.S. Appl. No. 13/795,276 dated Apr. 22, 2016.
U.S. Office Action for U.S. Appl. No. 13/795,276 dated Oct. 6, 2015.
U.S. Office Action for U.S. Appl. No. 13/802,896 dated Sep. 24, 2014.
U.S. Office Action for U.S. Appl. No. 13/803,958 dated Aug. 11, 2014.
U.S. Office Action for U.S. Appl. No. 13/803,958 dated May 28, 2015.
U.S. Office Action for U.S. Appl. No. 13/803,958 dated Nov. 18, 2015.
U.S. Office Action for U.S. Appl. No. 13/923,503 dated Mar. 22, 2016.
U.S. Office Action for U.S. Appl. No. 14/031,300 dated Jan. 20, 2016.
U.S. Office Action for U.S. Appl. No. 14/031,300 dated Jul. 7, 2015.
U.S. Office Action for U.S. Appl. No. 14/200,195 dated Mar. 21, 2016.
U.S. Office Action for U.S. Appl. No. 14/200,195 dated Nov. 4, 2015.
U.S. Office Action for U.S. Appl. No. 14/200,530 dated Feb. 29, 2016.
U.S. Office Action for U.S. Appl. No. 14/203,655 dated Aug. 10, 2016.
U.S. Office Action for U.S. Appl. No. 14/656,190 dated May 18, 2017.
U.S. Office Action for U.S. Appl. No. 14/656,657 dated Jul. 7, 2017.
U.S. Office Action for U.S. Appl. No. 14/686,452 dated Jun. 9, 2017.
U.S. Office Action for U.S. Appl. No. 14/843,944 dated Jun. 23, 2017.
U.S. Office Action for U.S. Appl. No. 14/856,471 dated May 31, 2017.
U.S. Office Action for U.S. Appl. No. 14/858,741 dated Dec. 1, 2016.
U.S. Office Action for U.S. Appl. No. 15/289,944 dated Feb. 9, 2017.
U.S. Office Action for U.S. Appl. No. 15/336,545 dated Dec. 19, 2016.
U.S. Office Action for U.S. Appl. No. 15/453,441 dated Jun. 5, 2017.
U.S. Office Action in U.S. Appl. No. 14/193,007 dated Apr. 24, 2017.
U.S. Office Action in U.S. Appl. No. 14/656,617 dated Apr. 4, 2017.
U.S. Office Action on U.S. Appl. No. 14/656,335 dated Apr. 25, 2017.

(56) References Cited

OTHER PUBLICATIONS

U.S. Office Action on U.S. Appl. No. 15/332,982 dated Jan. 30, 2017.
U.S. Supplemental Notice of Allowance for U.S. Appl. No. 13/795,276 dated Nov. 29, 2016.
Vallon, "Micropuncturing the nephron," Pflugers Archiv : European journal of physiology 458. 1 (May 2009): 189-201.
Van Der Zande et al. "Large-scale arrays of single-layer graphene resonators." Nano letters 10.12 (2010): 4869-4873.
Verdonck, P., "Plasma Etching", in Oficina de Microfabricao: Projeto e Construcao de Ci's MOS, Swart, J.W., Ed., Campinas (Sao Paulo, Brazil): UNICAMP, 2006, ch. 10, p. 9.
Vlassiouk et al. "Large scale atmospheric pressure chemical vapor deposition of graphene." Carbon 54 (2013): 58-67.
Vriens et al. "Methodological considerations in quantification of oncological FDG PET studies." European journal of nuclear medicine and molecular imaging 37.7 (2010): 1408-1425.
Wang et al., "Direct Observation of a Long-Lived Single-Atom Catalyst Chiseling Atomic Structures in Graphene," Nano Lett., 2014, pp. A-F.
Wang et al., "Porous Nanocarbons: Molecular Filtration and Electronics," Advances in Graphene Science, Edited by Mahmood Aliofkhazraei, (2013) ISBN 978-953-51-1182-5, Publisher: InTech; Chapter 6, pp. 119-160.
Wang et al., "What is the role of the second "structural " NADP+-binding site in human glucose 6-phosphate dehydrogenase?," Protein science a publication of the Protein Society 17. 8 (Aug. 2008): 1403-11.
Wei et al., "Synthesis of N-doped graphene by chemical vapor deposition and its electrical properties", Nano Lett. 2009 9 1752-58.
Xiaogan Liang et al., Formation of Bandgap and Subbands in Graphene Nanomeshes with Sub-10nm Ribbon Width Fabricated via Nanoimprint Lithography., Nano Letters, Jun. 11, 2010, pp. 2454-2460.
Xie et al., "Fractionation and characterization of biologically-active polysaccharides from Artemisia tripartite," Phytochemistry 69. 6 (Apr. 2008): 1359-71.
Xie, et al. "Controlled fabrication of high-quality carbon nanoscrolls from monolayer graphene." Nano letters 9.7 (2009): 2565-2570.
Yagil et al. "Nonproteinuric diabetes-associated nephropathy in the Cohen rat model of type 2 diabetes" Diabetes 54. 5 (May 2005): 1487-96.
Zan et al. "Interaction of Metals with Suspended Graphene Observed by Transmission Electron Microscopy", J. Phys. Chem. Lett., Mar. 8, 2012, 3, 953-958.
Zhang et al. "Effect of Chemical Oxidation on the Structure of Single-Walled Carbon Nanotubes", J. Phys. Chem., Feb. 12, 2003, B 107 3712-8.
Zhang et al. "Method for anisotropic etching of graphite or graphene" Institute of Physics, Chinese Academy of Sciences; PEOP. Rep. China; Mar. 30, 2011.
Zhang et al. "Production of Graphene Sheets by Direct Dispersion with Aromatic Healing Agents", Small, May 6, 2010, vol. 6, No. 10, 1100-1107.
Zhang et al. "Isolation and activity of an alpha-amylase inhibitor from white kidney beans," Yao xue xue bao =Acta pharmaceutica Sinica 42. 12 (Dec. 2007): 1282-7.
Zhao, et al. "Efficient preparation of large-area graphene oxide sheets for transparent conductive films." ACS nano 4.9 (2010): 5245-5252.
Zhou, K., et al., "One-pot preparation of graphene/ Fe304 composites by a solvothermal reaction," New J. Chem., 2010, 34, 2950.
Zhu et al. "Carbon Nanotubes in Biomedicine and Biosensing", Carbon Nanotubes-Growth and Applications, InTech, (Aug. 9, 2011) Chapter 6: pp. 135-162. Available from: https://www.intechopen.com/books/carbon-nanotubes-growth-and-applications/carbon-nanotubes-in-biomedicine-and-biosensing.
Ziegelmeier et al. "Adipokines influencing metabolic and cardiovascular disease are differentially regulated in maintenance hemodialysis," Metabolism: clinical and experimental 57. 10 (Oct. 2008): 1414-21.
Zirk et al. "A refractometry-based glucose analysis of body fluids," Medical engineering & physics 29. 4 (May 2007): 449-58.
Zyga "Nanoporous Graphene Could Outperform Best Commercial Water Desalination Techniques," Phys.org., Jun. 22, 2012, Retrieved from http://www.phys.org/pdf259579929.pdf [Last Accessed Dec. 3, 2014] (3 pages).
Dong et al., "Growth of large-sized graphene thin-films by liquid precursor-based chemical vapor deposition under atmospheric pressure," Carbon 49(11): 3672-3678 (May 2011).
Hong et al., "Graphene multilayers as gates for multi-week sequential release of proteins from surfaces," NIH-PA Author Manuscript PMC (Jun. 1, 2014), also published in ACS Nano, Jan. 24, 2012; 6(1): 81-88 (first published online Dec. 29, 2011).
Hu et al., "Enabling graphene oxide nanosheets as water separation membranes," Environmental Science & Technology, 47(8): 3715-3723 (Mar. 14, 2013).
International Search Report and Written Opinion of the International Searching Authority dated Jul. 22, 2016, from related international patent application PCT/US2016/027607.
International Search Report and Written Opinion of the International Searching Authority dated Jul. 22, 2016, from related international patent application PCT/US2016/027616.
International Search Report and Written Opinion of the International Searching Authority dated Jul. 22, 2016, from related PCT application PCT/US2016/027596.
International Search Report and Written Opinion of the International Searching Authority dated Jul. 22, 2016, from related PCT application PCT/US2016/027603.
International Search Report and Written Opinion of the International Searching Authority dated Jul. 22, 2016, from related PCT application PCT/US2016/027610.
International Search Report and Written Opinion of the International Searching Authority dated Jul. 22, 2016, from related PCT application PCT/US2016/027612.
International Search Report and Written Opinion of the International Searching Authority dated Jun. 22, 2016, from related PCT application PCT/US2016/027637.
Kurapati et al., "Graphene oxide based multilayer capsules with unique permeability properties: facile encapsulation of multiple drugs," Chemical Communication 48: 6013-6015 (Apr. 25, 2012).
Li et al., "3D graphene oxide-polymer hydrogel: near-infrared light-triggered active scaffold for reversible cell capture and on-demand release," Advanced Materials 25: 6737-6743 (Oct. 7, 2013).
Marquardt et al., "Hybrid materials of platinum nanoparticles and thiol-functionalized graphene derivatives," Carbon 66: 285-294 (Jan. 2014; first published online Sep. 12, 2013).
Nam et al., "Monodispersed PtCo nanoparticles on hexadecyltrimethylammonium bromide treated graphene as an effective oxygen reduction reaction catalyst for proton exchange membrane fuel cells," Carbon 50: 3739-3747 (Aug. 2012; first published online Apr. 5, 2012).
Nandamuri et al., "Chemical vapor deposition of graphene films," Nanotechnology 21(14): 1-4 (Mar. 10, 2010).
Nayini et al., "Synthesis and characterization of functionalized carbon nanotubes with different wetting behaviors and their influence on the wetting properties of carbon nanotubes/polymethylmethacrylate coatings," Progress in Organic Coatings 77(6): 1007-1014 (Mar. 2014).
Sun et al., "Growth of graphene from solid carbon sources," Nature 468(7323): 549-552 (Nov. 25, 2010; including corrigendum in Nature 471(7336): 124 (Mar. 2011).
Tang et al., "Highly wrinkled cross-linked graphene oxide membranes for biological and charge-storage applications," Small 8(3): 423-431 (Feb. 6, 2012; first published online Dec. 13, 2011).
Notice of Allowance for U.S. Appl. No. 14/819,273 dated Oct. 28, 2016.
U.S. Office Action for U.S. Appl. No. 14/193,007 dated Oct. 21, 2016.

(56) References Cited

OTHER PUBLICATIONS

U.S. Office Action for U.S. Appl. No. 14/193,007 dated Dec. 21, 2015.
U.S. Office Action for U.S. Appl. No. 14/193,007 dated Jul. 1, 2016.
U.S. Notice of Allowance in U.S. Appl. No. 14/610,770 dated Jan. 23, 2017.
U.S. Notice of Allowance in U.S. Appl. No. 14/856,198 dated Feb. 10, 2017.
U.S. Notice of Allowance in U.S. Appl. No. 14/856,198 dated Mar. 1, 2017.
U.S. Office Action in U.S. Appl. No. 14/609,325 dated Feb. 16, 2017.
U.S. Office Action in U.S. Appl. No. 14/193,007 dated Mar. 23, 2017.
U.S. Office Action in U.S. Appl. No. 14/656,580 dated Feb. 9, 2017.
U.S. Office Action in U.S. Appl. No. 14/843,944 dated Jan. 6, 2017.
U.S. Office Action in U.S. Appl. No. 15/099,464 dated Mar. 10, 2017.
Barreiro et al. "Understanding the catalyst-free transformation of amorphous carbon into graphene by current-induced annealing," Scientific Reports, 3 (Article 1115): 1-6 (Jan. 2013).
Botari et al., "Graphene healing mechanisms: A theoretical investigation," Carbon, 99: 302-309 (Apr. 2016) (published online Dec. 2015).
Chen et al., "Defect Scattering in Graphene," Physical Review Letters, 102: 236805-1-236805-4 (Jun. 2009).
Chen et al., "Self-healing of defected graphene," Applied Physics Letters, 102(10): 103107-1-103107-5 (Mar. 2013).
Cheng et al., "Ion Transport in Complex Layered Graphene-Based Membranes with Tuneable Interlayer Spacing," Science Advances, 2(2): e1501272 (9 pages) (Feb. 2016).
Crock et al., "Polymer Nanocomposites with Graphene-Based Hierarchical Fillers as Materials for Multifunctional Water Treatment Membranes," Water Research, 47(12): 3984-3996 (Aug. 2013) (published online Mar. 2013).
Han et al., "Ultrathin Graphene Nanofiltration Membrane for Water Purification," Advanced Functional Materials, 23(29): 3693-3700 (Aug. 2013).
International Search Report and Written Opinion in PCT/US2016/027583 dated Jan. 13, 2017.
Written Opinion in PCT/US2016/027590 dated Jan. 6, 2017.
International Search Report and Written Opinion in PCT/US2016/027594 dated Jan. 13, 2017.
International Search Report and Written Opinion in PCT/US2016/027628 dated Jan. 9, 2017.
International Search Report and Written Opinion in PCT/US2016/027631 dated Jan. 13, 2017.
International Search Report and Written Opinion in PCT/US2016/027632 dated Jan. 9, 2017.
Written Opinion in PCT/US2016/052010 dated Dec. 20, 2016.
International Search Report in PCT/US2016/027629 dated Dec. 8, 2016.
International Search Report in PCT/US2016/052007 dated Dec. 27, 2016.
Kjeldsen, T., "Yeast secretory expression of insulin precursors," Appl Microbiol Biotechnol, 54: 277-286 (May 2000).
Lin et al., "A Direct and Polymer-Free Method for Transferring Graphene Grown by Chemical Vapor Deposition to Any Substrate," ACSNANO, 8(2): 1784-1791 (Jan. 2014).
Liu et al. "Synthesis of high-quality monolayer and bilayer graphene on copper using chemical vapor deposition," Carbon, 49(13): 4122-4130 (Nov. 2011) (published online May 2011).
O'Hern et al., "Nanofiltration across defect-sealed nanoporous monolayer graphene," Nano Letters, 15(5): 3254-3260 (Apr. 2015).
U.S. Corrected Notice of Allowance in U.S. Appl. No. 13/480,569 dated May 26, 2015.
U.S. Notice of Allowance for U.S. Appl. No. 14/610,770 dated Apr. 25, 2016.
U.S. Notice of Allowance in U.S. Appl. No. 14/819,273 dated Dec. 14, 2016.
U.S. Notice of Allowance in U.S. Appl. No. 13/480,569 dated Feb. 27, 2015.
U.S. Office Action in U.S. Appl. No. 13/480,569 dated Jul. 30, 2014.
U.S. Office Action in U.S. Appl. No. 14/856,471 dated Dec. 1, 2016.
U.S. Restriction Requirement in U.S. Appl. No. 14/193,007 dated Jul. 17, 2015.
Wang et al., "Graphene Oxide Membranes with Tunable Permeability due to Embedded Carbon Dots," Chemical Communications, 50(86): 13089-13092 (Nov. 2014) (published online Sep. 2014).
Xu et al., "Graphene Oxide-$TiO_2$ Composite Filtration Membranes and their Potential Application for Water Purification," Carbon, 62: 465-471 (Oct. 2013) (published online Jun. 2013).
Zhao et al., "A glucose-responsive controlled release of insulin system based on enzyme multilayers-coated mesoporous silica particles," Chem. Commun., 47: 9459-9461 (Jun. 2011).
International Search Report dated Dec. 4, 2015, in related international application PCT/US2015/048205.
International Search Report dated Jun. 10, 2015, from related international application PCT/US15/20201.
EPO Extended Search Report for European Application No. 171684883.5 dated Jul. 25, 2017 (8 pages).
EPO Supplementary Search Report for European Application No. 15762019.6 dated Aug. 9, 2017 (16 pages).
U.S. Notice of Allowance in U.S. Appl. No. 14/610,770 dated Sep. 26, 2017. (12 pages).
U.S. Notice of Allowance in U.S. Appl. No. 15/332,982 dated Sep. 21, 2017. (5 pages).
U.S. Office Action in U.S. Appl. No. 15/099,099 dated Oct. 5, 2017 (11 pages).
U.S. Office Action in U.S. Appl. No. 15/099,447 dated Oct. 3, 2017 (21 pages).
Weisen, et al., "Fabrication of nanopores in a graphene sheet with heavy ions: A molecular dynamics study", Journal of Applied Physics 114, 234304 (2013), pp. 234304-1 to 234304-6.
CN Office Action in Chinese Application No. 201580006829.5 dated Aug. 1, 2017. (English translation) (8 pages).
EP Office Action for European Application No. 15743307.9 dated Aug. 8, 2017. (17 pages).
European Search Report dated Aug. 28, 2017 from related EP application 15743750.0. (7 pages).
International Search Report and Written Opinion dated Aug. 14, 2017 from related PCT application PCT/US2017/031537. (12 pages).
Jiang, L. et al., Design of advanced porous grapheme materials: from grapheme nanomesh to 3D architectures. Nanoscale, Oct. 16, 2013, vol. 6, pp. 1922-1945.
JP Office Action in Japanese Application No. 2015-503405 dated Jun. 28, 2017. (English translation) (6 pages).
JP Office Action in Japanese Application No. 2015-549508 dated Jun. 27, 2017. (English translation) (7 pages).
Li, R.H. "Materials for immunoisolated cell transplantation". Adv. Drug Deliv. Rev. 33, 87-109 (1998). (23 pages).
Schweitzer, Handbook of Separation Techniques for Chemical Engineers, 1979, McGraw-Hill Book Company, pp. 2-5 to 2-8.
Search Report and Written Opinion dated Aug. 14, 2017 for Singapore Application No. 11201606287V. (10 pages).
Search Report and Written Opinion dated Aug. 22, 2017 for Singapore Application No. 11201607584P. (7 pages).
Sears et al., "Recent Developments in Carbon Nanotube Membranes for Water Purification and Gas Separation" Materials, vol. 3 (Jan. 4, 2010), pp. 127-149.
U.S. Notice of Allowance in U.S. Appl. No. 14/193,007 dated Sep. 6, 2017. (9 pages).
U.S. Notice of Allowance in U.S. Appl. No. 14/656,580 dated Sep. 5, 2017. (8 pages).
U.S. Office Action for U.S. Appl. No. 14/609,325 dated Aug. 25, 2017. (7 pages).
U.S. Office Action for U.S. Appl. No. 15/099,193 dated Jul. 19, 2017. (13 pages).
U.S. Office Action for U.S. Appl. No. 15/289,944 dated Jul. 13, 2017. (18 pages).
U.S. Office Action for U.S. Appl. No. 15/332,982 dated Aug. 18, 2017. (9 pages).

(56) References Cited

OTHER PUBLICATIONS

Australian Office Action in Application No. 2013235234 dated Dec. 19, 2017 (5 pages).
Japanese Office Action in Application No. 2017-002652 dated Nov. 24, 2017 (with English translation) (7 pages).
Chu, L., et al., "Porous graphene sandwich/poly(vinylidene fluoride) composites with high dielectric properties," Composites Science and Technology, 86, (2013), pp. 70-75.
European Extended Search Report in Application No. 15743307.9 dated Nov. 15, 2017 (14 pages).
European Extended Search Report in Application No. 15755350.4 dated Oct. 30, 2017 (9 pages).
European Extended Search Report in Application No. 15762019.6 dated Nov. 20, 2017 (12 pages).
European Extended Search Report in Application No. 15762213.5 dated Oct. 10, 2017 (8 pages).
Gu et al., "One-step synthesis of porous graphene-based hydrogels containing oil droplets for drug delivery", Royal Society of Chemistry (RSC), vol. 4, No. 7, Jan. 1, 2014, pp. 3211-3218.
Japanese Office Action in Application No. 2015-549508 dated Nov. 7, 2017 (with English translation) (2 pages).
Kim et al., "Selective Gas Transport Through Few-Layered Graphene and Graphene Oxide Membranes", Science, vol. 342, Oct. 4, 2013, pp. 91-95 (6 total pages).
Singapore Search Report and Written Opinion in Application No. 11201609272T dated Oct. 5, 2017 (11 pages).
U.S. Notice of Allowance in U.S. Appl. No. 15/099,464 dated Nov. 16, 2017 (5 pages).
U.S. Notice of Allowance in U.S. Appl. No. 15/332,982 dated Nov. 1, 2017 (9 pages).
U.S. Office Action in U.S. Appl. No. 14/707,808 dated Nov. 6, 2017 (27 pages).
U.S. Office Action in U.S. Appl. No. 15/099,193 dated Dec. 28, 2017 (25 pages).
U.S. Office Action in U.S. Appl. No. 15/099,304 dated Nov. 24, 2017 (23 pages).
Wang, M., et al., "Interleaved Porous Laminate Composed of Reduced Graphene Oxide Sheets and Carbon Black Spacers by In-Situ Electrophoretic Deposition," The Royal Society of Chemistry (2014), pp. 1-3.
Wimalasiri, Y., et al., "Carbon nanotube/graphene composite for enhanced capacitive deionization performance," Carbon 59 (2013), pp. 464-471.
Bose et al.,"Microfabricated immune-isolating devices for transplanting therapeutic cells in vivo", Koch Institute of Integrative Cancer Research, Massachusetts Institute of Technology, Undated (1 page).
Indian Office Action for Appl. Ser. No. 7731/DELNP/2014 dated Jul. 26, 2018 (6 pages).
Japanese Office Action for Appl. Ser. No. 2017-002652 dated Jul. 3, 2018 (8 pages).
Linnert, "Welding Metallurgy—Carbon and Alloy Steels", vol. I—Fundamentals (4th Edition), Chapter 2—The Structure of Metals, GML Publications, American Welding Society (AWS), Year: 1994, pp. 17-74. Retrieved from app.knovel.com/hotlink/pdf/id:kt0095RCL3/welding-metallurgy-carbon/structure-metals.
U.S. Final Office Action for U.S. Appl. No. 14/707,808 dated Jun. 27, 2018 (28 pages).
U.S. Final Office Action for U.S. Appl. No. 15/099,482 dated Aug. 27, 2018 (10 pages).
U.S. Non-Final Office Action for U.S. Appl. No. 15/099,239 dated Jul. 12, 2018 (31 pages).
U.S. Non-Final Office Action for U.S. Appl. No. 15/099,304 dated Aug. 27, 2018 (22 pages).
U.S. Notice of Allowance for U.S. Appl. No. 15/099,420 dated Aug. 8, 2018 (8 pages).
Vatanpour et al., "Fabrication and characterization of novel antifouling nanofiltration membrane prepared from oxidized multiwalled carbon nanotube/polyethersulfone nanocomposite", Journal of Membrane Science, vol. 375, Elsevier, Apr. 6, 2011, pp. 284-294.
Zhang et al., "Synergetic effects of oxidized carbon nanotubes and graphene oxide on fouling control and anti-fouling mechanism of polyvinylidene fluoride ultrafiltration membranes", Journal of Membrane Science, vol. 448, Elsevier, Aug. 7, 2013, pp. 81-92.
European Extended Search Report in Application No. 15837617.8 dated Mar. 22, 2018 (9 pages).
Singapore Written Opinion for Appl. Ser. No. 11201607584P dated Jun. 8, 2018 (7 pages).
U.S. Non-Final Office Action for U.S. Appl. No. 15/099,410 dated Jun. 13, 2018 (15 pages).
U.S. Notice of Allowance for U.S. Appl. No. 15/453,441 dated Jun. 12, 2018 (8 pages).
U.S. Office Action for U.S. Appl. No. 15/099,289 dated Jun. 7, 2018 (16 pages).
US Final Office Action for U.S. Appl. 14/609,325 dated Sep. 12, 2018 (8 pages).
US Final Office Action for U.S. Appl. No. 15/099,289 dated Oct. 15, 2018 (14 pages).
US Non-Final Office Action for U.S. Appl. No. 14/656,657 dated Oct. 10, 2018 (6 pages).
US Non-Final Office Action for U.S. Appl. No. 14/707,808 dated Nov. 15, 2018 (34 pages).
US Non-Final Office Action for U.S. Appl. No. 15/099,099 dated Sep. 27, 2018 (13 pages).
US Non-Final Office Action for U.S. Appl. No. 15/099,269 dated Oct. 5, 2018 (11 pages).
US Non-Final Office Action for U.S. Appl. No. 15/099,276 dated Nov. 1, 2018 (13 pages).

* cited by examiner

A

B

METHODS FOR IN SITU MONITORING AND CONTROL OF DEFECT FORMATION OR HEALING

BACKGROUND

Graphene represents a form of carbon in which the carbon atoms reside within a single atomically thin sheet or a few layered sheets (e.g., about 20 or less) of fused six-membered rings forming an extended planar lattice. In its various forms, graphene has garnered widespread interest for use in a number of applications, primarily due to its favorable combination of high electrical and thermal conductivity values, good in-plane mechanical strength, and unique optical and electronic properties. Of particular interest to industry are large-area graphene films for applications such as, for example, special barrier layers, coatings, large area conductive elements (e.g., RF radiators or antennas), integrated circuits, transparent electrodes, solar cells, gas barriers, flexible electronics and the like.

Some envisioned applications for graphene and other two-dimensional materials are predicated upon introducing defects, such as forming a plurality of nanometer-scale holes in the planar structure. For example, the hole density of perforated graphene can be used to tune the electrical conductivity of this nanomaterial and in some instances can be used to adjust its electronic band structure. Filtration applications are another area where perforated graphene and other perforated two-dimensional materials have generated considerable interest. Due to the atomic-level thinness of graphene and other two-dimensional materials, it is possible to achieve high fluid throughput fluxes during filtration processes.

A number of processes are known for perforating and/or defecting graphene and other two-dimensional materials (e.g., ion bombardment, oxidation, nanoparticle bombardment, etc.). Likewise, a number of techniques for healing holes, that are too large for a given application, in graphene and other two-dimensional materials have been disclosed (see, for example, US patent application filed herewith, entitled METHOD FOR MAKING TWO-DIMENSIONAL MATERIALS AND COMPOSITE MEMBRANES THEREOF HAVING SIZE-SELECTIVE PERFORATIONS, U.S. Pat No. 15/099,482 incorporated herein in its entirety). However, production of holes with a desired size range, a narrow size distribution, and a high and uniform hole density remains a challenge, at least partially, due to small physical and chemical inconsistencies from sheet-to-sheet of the two-dimensional material (e.g. layers, intrinsic or native defects, strain, electron distribution and crystallinity) and surface contamination. Currently, there is no way to monitor and adjust perforation or healing conditions in real-time. Instead, samples are perforated or healed, then tested by a separate process, and perforation or healing parameters are adjusted and applied to a new sheet of material, which inevitably possesses chemical and physical variations that cause it to respond differently to the new conditions. For example, contamination from sample to sample may vary, and needs to be accounted for. Typically to validate a perforation process, graphene needs to be transferred simultaneously to multiple TEM grids and to a desired support substrate. The TEM grids are then exposed to various different treatments. These must then be individually loaded into an STEM and imaged to determine the perforation results. If one of the conditions turns out to be appropriate, the the graphene on the support substrate is then subjected to the same treatment.

In view of the foregoing, methods that monitor and adjust for inter- and intra-sheet variability during perforation or healing of graphene and other two-dimensional materials would be of considerable interest in the art. In particular, methods for real-time, in situ monitoring of defect formation or healing would be of considerable interest in the art. For example, monitoring of defect formation or healing for suspended graphene would be of interest. The present disclosure satisfies the foregoing needs and provides related advantages as well.

SUMMARY

This disclosure provides methods for monitoring a variety of perforation and healing procedures via monitoring schemes that provide real-time feedback, while defects are being produced or healed. The invention describes several detection mechanisms that provide in situ or substantially simultaneous feedback on defect production or healing either locally or globally for a graphene or two-dimensional sheet. The feedback data can be used to adjust perforation or healing parameters, such as the total dose or efficacy of the perforating radiation, to achieve the desired defect state. This method advantageously accounts for inter- and intra-sheet chemical and physical variability. Variability may arise from varying substrate/graphene interaction. For example, variability may arise from nanoparticles (NPs) perforating graphene differently in some instances, such as when the area of the substrate pore that the NP spans changes. This method advantageously accounts for this variance in the perforation system, and monitors, for example, defects created by NPs perforating the substrate.

In an aspect, a method for monitoring defect formation or healing comprises: exposing a surface of a material to incident radiation; detecting scattered, emitted or transmitted radiation from at least a portion of the material exposed to the incident radiation; and generating data indicative of defect formation or healing, wherein the method is performed in situ and the data indicative of defect formation or healing provides a rate of defect formation or healing, a temporal change in the rate of defect formation or healing, a temporal change in the size of the defects, a spatial change in the rate of defect formation or healing, a spatial change in the size of the defects, or combinations thereof. As described herein the incident radiation, and the scattered, emitted or transmitted radiation may be any one or more of electromagnetic radiation, electrons, ions, nanoparticles, or plasma. In an embodiment, incident radiation is processing radiaton, such as perforating or healing radiation or interrogating radiation. The incident radiation may also be both processing radiation and interrogating radiation. As described herein, processing radiation performs a process on the material when incident thereon.

In an embodiment, the step of generating data indicative of defect formation comprises determining secondary electron yield.

In an embodiment, the step of exposing the surface of the material to incident radiation produces a plurality of defects in the material.

In an embodiment, the step of detecting radiation or particles comprises: (i) performing secondary ion mass spectroscopy; (ii) performing Raman spectroscopy; (iii) performing residual gas analysis on particles being removed from the material; (iv) detecting back scattered radiation or particles; (v) detecting Auger electrons; (vi) performing scanning probe microscopy; (vii) performing scanning tunneling microscopy; (viii) performing atomic force microscopy; (ix) performing X-ray photoelectron spectroscopy; (x) performing transmission electron microscopy; (xi) detecting nanoparticles on one or more microbalances or Faraday cups positioned behind the material; (xii) performing small angle electron diffraction; (xiii) detecting nanoparticles on a surface positioned behind the material using surface enhanced Raman scattering (SERS); (xiv) detecting secondary electrons; (xv) detecting transmitted electron or ions; or (xvi) performing a combination of two or more of (i)-(xv). In an embodiment, the back scattered radiation or particles are selected from the group consisting of electrons, protons and helium. In an embodiment, scattered radiation or particles are selected from the group consisting of electrons, protons, helium, gallium, neon, argon, xenon, or ions.

In an embodiment, the steps of exposing and detecting occur simultaneously.

In an embodiment, the incident radiation and the scattered, emitted or transmitted radiation are the same type of radiation or different types of radiation. In an embodiment, the scattered, emitted or transmitted radiation results from the incident radiation or an additional source of interrogating radiation.

In an embodiment, the scattered, emitted or transmitted radiation from the material is collected from a bulk portion of the surface having an area between 1 $\mu m^2$ and 1000 $cm^2$. In an embodiment, the scattered, emitted or transmitted radiation from the material is collected from a local portion of the surface having an area between 100 $nm^2$ and 10 $mm^2$.

In an embodiment, the scattered, emitted or transmitted radiation is continuously collected. In an alternate embodiment, the incident radiation is pulsed and the scattered, emitted or transmitted radiation is collected only when the incident radiation is off. As noted above, the incident radiation, and the scattered, emitted or transmitted radiation may be any one or more of electromagnetic radiation, electrons, ions, nanoparticles, or plasma.

In an embodiment the emitted radiation is secondary electrons. The secondary electrons could be generated by electrons or ions, for example.

Methods for monitoring defect formation or healing via gas permeation are also contemplated. For example, in an aspect, a method for monitoring defect formation or healing comprises: exposing a surface of a analyte to incident radiation; detecting movement of an analyte through defects in the material; and generating data indicative of defect formation or healing, wherein the method is performed in situ and the data indicative of defect formation or healing provide a rate of defect formation or healing, a temporal change in the rate of defect formation or healing, a temporal change in the size of the defects, a spatial change in the rate of defect formation or healing, a spatial change in the size of the defects, a maximum size of the defects, a number of pores, or combinations thereof.

In an embodiment, the step of detecting movement of the analyte through the defects in the material comprises one or more of: (i) determining the presence or absence of the analyte at a detector; (ii) quantifying the analyte; (iii) identifying a composition, mass, average radius, charge or size of the analyte; (iv) determining a rate of movement of the analyte through the defects in the material; or (v) a combination of two or more of (i)-(iv). In an embodiment, the analyte is a gas selected from the group consisting of hydrogen, helium, oxygen, nitrogen, xenon, neon, argon, $SF_6$, $H_2O$, $C_xH_{2x}$ where x is 1 to 4, and combinations thereof. In an embodiment, the analyte is a plasma. In an embodiment, the incident radiation is a plasma, potentially capable of perforating or modifying the two-dimensional material, and the analyte is one or more species of the plasma. For example, the one or more species of the plasma may be a charged species.

Methods for monitoring defect formation or healing via electrical biasing are also contemplated. For example, in an aspect, a method for monitoring defect formation or healing, comprises: exposing a surface of the material to incident radiation; applying an electrical bias to the material; measuring electrical conductivity through a conductive probe in electrical contact with the material; and generating data indicative of defect formation or healing, wherein the method is performed in situ and the data indicative of defect formation or healing provide a rate of defect formation or healing, a temporal change in the rate of defect formation or healing, a temporal change in the size of the defects, a spatial change in the rate of defect formation or healing, a spatial change in the size of the defects, or combinations thereof. In an embodiment, a conductive probe is a conductive grid or a local probe. In an embodiment, defect density and electrical conductivity are inversely related such that an increase in defect density is observed as a decrease in electrical conductivity. In an embodiment the electrical conductivity of the material changes as a result of the defects. Further, defects in graphene other than holes may be beneficial for being detected based on electronic properties in a number of applications. For example, disrupting the graphene lattice and making 5 and 7 member rings, instead of the typical 6 member rings, can beneficially change the electronic properties of graphene. Likewise, doping of the graphene can also be beneficial, for example substituting boron, nitrogen, or silicon atoms in graphene can change the electrical properties sufficiently to be detected.

Methods for monitoring defect formation or healing via heating are also contemplated. For example, in an aspect, a method for monitoring defect formation or healing, comprises: exposing a surface of a material to incident radiation; heating the material; subsequently measuring temperature of the surface of the material; and generating data indicative of defect formation or healing, wherein the method is performed in situ and the data indicative of defect formation or healing provides a rate of defect formation or healing, a temporal change in the rate of defect formation or healing, a temporal change in the size of the defects, a spatial change in the rate of defect formation or healing, a spatial change in the size of the defects, or combinations thereof. In an embodiment, the step of heating the material comprises applying a potential to the two-dimensional material to induce joule heating. In an embodiment, defect density and thermal conductivity are inversely related such that an increase in defect density is observed as a decrease in thermal conductivity.

In an embodiment, the incident radiation is a particle beam. In an embodiment for monitoring a bulk portion of a material, the particle beam produces a spot on the surface of the material, the spot having an area between 1 $\mu m^2$ and 100 $cm^2$, or between 10 $\mu m^2$ and 10 $cm^2$. In an embodiment for monitoring a local portion of a material, the particle beam is a microbeam that produces a spot on the surface of the material, the spot having an area between 1 $nm^2$ and 1 $mm^2$, or between 10 $nm^2$ and 10 $\mu m^2$.

In an embodiment, the particle beam is an ion beam, where the ion beam has an ion energy of at least 20 eV, or at least 50 eV, or at least 100 eV. For example, the ion beam may have an ion energy selected from the range of 20 eV to 10 keV, or 20 eV to 1 keV, or 50 eV to 1 keV, or 100 eV to 1 keV. In an embodiment, the ion beam has a flux selected from the range of 10 $pA/mm^2$ to 1 $\mu A/mm^2$, or 10 $nA/mm^2$ to 10 mA/mm$^2$, or 50 nA/mm$^2$ to 5 mA/mm$^2$. In an embodiment, the surface of the material is exposed to an ion dose ranging from $1\times10^{11}$ ions/cm$^2$ to $1\times10^{20}$ ions/cm$^2$, or from $1\times10^{12}$ ions/cm$^2$ to $1\times10^{18}$ ions/cm$^2$, or from $1\times10^{12}$ ions/cm$^2$ to $1\times10^{15}$ ions/cm$^2$. In an embodiment, the ion beam comprises ions selected from the group consisting of He$^+$, Xe$^+$, Ne$^+$, Ar$^+$, Cs$^+$, Bi$^{3+}$, Au$^+$, Au$^{3+}$ and combinations thereof. In an embodiment, the ion beam comprises organic or organometallic ions having a molecular mass from 90 to 200. In an embodiment, the ion beam comprises ions selected from the group consisting of tropylium ions, ferrocenium ions and combinations thereof.

In an embodiment, the particle beam is an electron beam. For example, the electron beam has an energy of at least 10 eV, or at least 100 eV, or at least 1 keV. In an embodiment, the electron beam may be interrogating radiation having an energy selected from the range of 10 eV to 40 keV, or 100 eV to 20 keV, or 1 keV to 10 keV. In an embodiment, the electron beam may be perforating radiation having an energy greater than or equal to 84 keV in the case of pristine graphene, or may be lower when the graphene is not pristine, such as when the graphene has carbon atoms without 3 sp$^2$ bonds.

In an embodiment, the particle beam is a nanoparticle beam. For example, the nanoparticle beam has an energy of at least 1 keV per nanoparticle, or at least 2 keV per nanoparticle, or at least 10 keV per nanoparticle. In an embodiment, the nanoparticle beam has an energy selected from the range of 2 keV to 500 keV per nanoparticle, or 5 keV to 300 keV per nanoparticle, or 10 keV to 200 keV per nanoparticle. In an embodiment, the nanoparticle beam has a flux selected from the range of $1.6\times10^5$ nanoparticles/s·cm$^2$ to $1\times10^{15}$ nanoparticles/s·cm$^2$, or $1\times10^6$ nanoparticles/s·cm$^2$ to $1\times10^{12}$ nanoparticles/s·cm$^2$, or $1\times10^7$ nanoparticles/s·cm$^2$ to $1\times10^{10}$ nanoparticles/s·cm$^2$. In an embodiment, the surface of the material is exposed to a nanoparticle dose ranging from $1\times10^8$ nanoparticles/cm$^2$ to $1\times10^{12}$ nanoparticles/cm$^2$, or from $1\times10^9$ nanoparticles/cm$^2$ to $1\times10^{11}$ nanoparticles/cm$^2$. In an embodiment, the nanoparticle beam comprises atoms or molecules selected from the group consisting of metal nanoparticles, carbon nanoparticles, gas clusters, core shell nanoparticles and combinations thereof. In an embodiment, the nanoparticle beam comprises atoms or molecules having a molecular mass from 100 to 4,000,000, or from 190 to 2,000,000.

In an embodiment, the material is a two-dimensional material. For example, the two-dimensional material may be a single atomic layer thick. In an embodiment, the two-dimensional material has a thickness less than or equal to 100 Angstroms. In an embodiment, the two-dimensional material is selected from the group consisting of a graphene or graphene-based film, a transition metal dichalcogenide, α-boron nitride, silicene, germanene, and combinations thereof. In an embodiment, the two-dimensional material is disposed on or supported by a three-dimensional material. In an embodiment, the material comprises a stack of two or more sheets of two-dimensional material, wherein each sheet is a single atomic layer thick. In an embodiment, the size of the holes or defects in the two-dimensional material ranges from 1-50 nm, 1-30 nm, 1-20 nm, 1-10 nm or 3-10 nm. In an embodiment, the two-dimensional material is graphene or a graphene-based material.

In an embodiment, the defects are pores extending throughout a thickness of the material. For example, the pores may have an average characteristic dimension less than or equal to 1 nm. In an embodiment, the pores have an average characteristic dimension ranging from 0.3 nm to 100 nm, or from 0.5 nm to 10 nm. In an embodiment, in situ or substantially simultaneous feedback on defect production or healing may be provided either locally or globally on a graphene or other two-dimensional sheet. The feedback data can be used to adjust perforation or healing parameters, such as the total dose or efficacy of the perforating radiation, to achieve the desired defect state.

In an embodiment, a method of monitoring further comprises comparing the data indicative of defect formation or healing to a threshold range for the data; and adjusting an energy or amount of the incident radiation if the data is outside of the threshold range. In this case, the flux, energy, sample temperature, background gas pressure could be changed, as well as the incidence angle.

In an embodiment, in situ or substantially simultaneous feedback on defect production or healing may be provided either locally or globally on a graphene or other two-dimensional sheet. The feedback data can be used to adjust perforation or healing parameters, such as the total dose or efficacy of the perforating radiation, to achieve the desired defect state.

In an embodiment, a method of monitoring defect formation or healing further comprises translating the material being defected or healed along a processing stage at a rate dependent upon a rate of defect formation or healing. The rate would depend on flux and energy of the incident radiation. In an embodiment, the fluence delivered to the material may be controlled by the rate at which the material is translated relative to the irradiating beam. In an embodiment, the ions from irradiating beam may be stopped from impinging on the surface of the sample by adjusting the bias on the material up to the ion accelerating voltage to stop the ions.

The foregoing has outlined rather broadly the features of the present disclosure in order that the detailed description that follows can be better understood. Additional features and advantages of the disclosure will be described hereafter. These and other advantages and features will become more apparent from the following description.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure.

DETAILED DESCRIPTION

Figure 1:
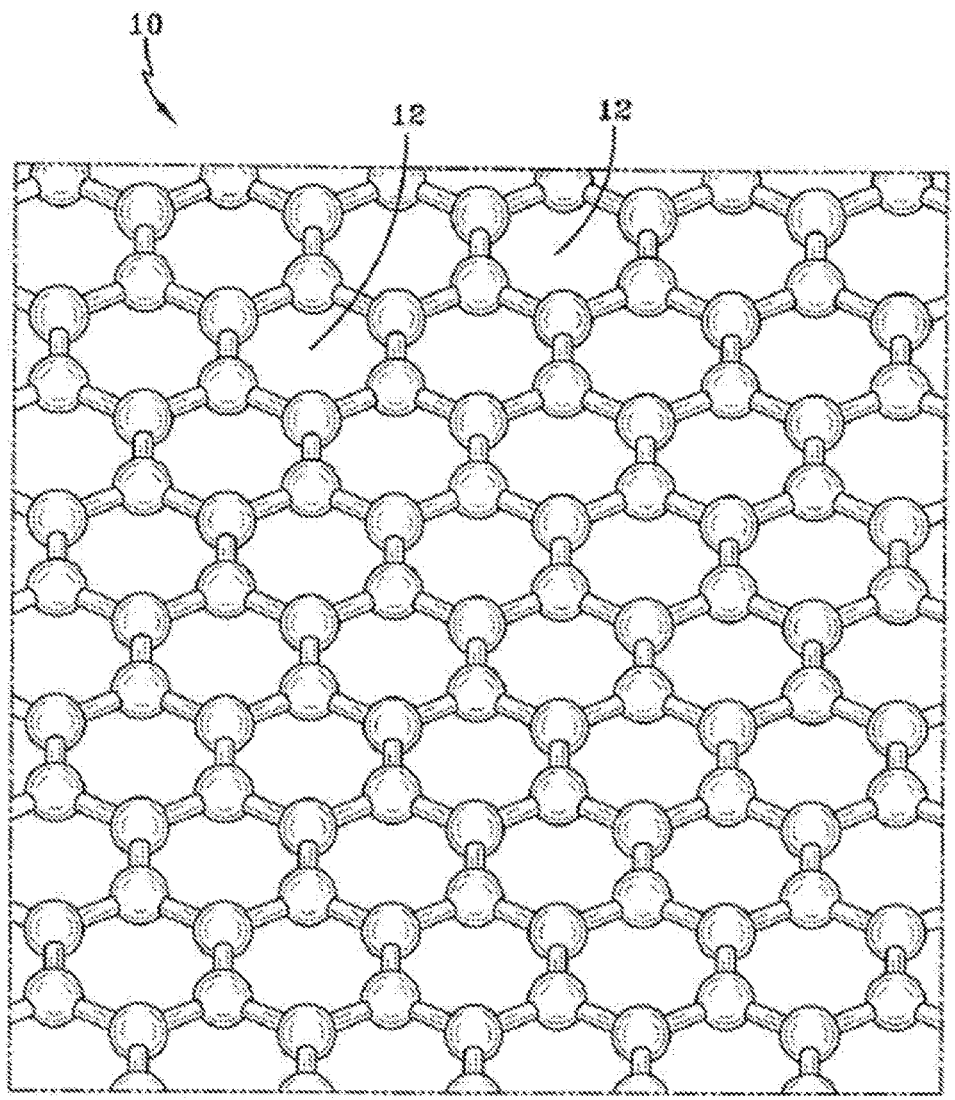
FIG. 1 is a schematic of graphene, which may be a two-dimensional material monitored by methods herein.

Graphene has garnered widespread interest for use in a number of applications due to its favorable mechanical and electronic properties, as well as its chemical inertness. Graphene represents an atomically thin two-dimensional layer of carbon in which the carbon atoms reside as closely spaced atoms at regular lattice positions. The regular lattice positions can have a plurality of defects present therein, which can occur natively or be intentionally introduced to the graphene basal plane. Such defects will also be equivalently referred to herein as "apertures," "perforations" or "holes." The term "perforated graphene" is used herein to denote a graphene sheet with defects in its basal plane, regardless of whether the defects are natively present or intentionally produced. Aside from such apertures, graphene and other two-dimensional materials can represent an impermeable layer to many substances. Therefore, when sized properly, the apertures in the impermeable layer of such materials can be useful for filtration and sequestration, for example.

Two-dimensional materials are, most generally, those which are atomically thin, with thickness ranging from single-layer sub-nanometer thickness to a few nanometers, and which generally have a high surface area. Two-dimensional materials include metal chalogenides (e.g., transition metal dichalogenides), transition metal oxides, hexagonal boron nitride, graphene, silicene and germanene (see: Xu et al. (2013) "Graphene-like Two-Dimensional Materials) Chemical Reviews 113:3766-3798). Graphene represents a form of carbon in which the carbon atoms reside within a single atomically thin sheet or few layered sheets (e.g., about 20 or less) of covalently bound carbon atoms forming an extended $sp^2$-hybridized planar lattice. In its various forms, graphene has garnered widespread interest for use in a number of applications, primarily due to its favorable combination of high electrical and thermal conductivity values, good in-plane mechanical strength, and unique optical and electronic properties. Other two-dimensional materials having a thickness of a few nanometers or less and an extended substantially planar lattice are also of interest for various applications. In an embodiment, a two dimensional material has a thickness of 0.3 to 1.2 nm. In other embodiments, a two dimensional material has a thickness of 0.3 to 3 nm.

In various embodiments, the two-dimensional material comprises a sheet of a graphene-based material. In an embodiment, the sheet of graphene-based material is a sheet of single- or multi-layer graphene or a sheet comprising a plurality of interconnected single- or multi-layer graphene domains. In embodiments, the multilayer graphene domains have 2 to 5 layers or 2 to 10 layers. In an embodiment, the layer comprising the sheet of graphene-based material further comprises non-graphenic carbon-based material located on the surface of the sheet of graphene-based material. In an embodiment, the amount of non-graphenic carbon-based material is less than the amount of graphene. In embodiments, the amount of graphene in the graphene-based material is from 60% to 95% or from 75% to 100%. In an embodiment, the amount of graphene in the graphene-based material is measured as an atomic percentage.

In embodiments, the characteristic size of the perforations of a perforated graphene, graphene-based or two-dimensional material is from 0.3 to 10 nm, from 1 to 10 nm, from 5 to 10 nm, from 5 to 20 nm, from 10 nm to 50 nm, from 50 nm to 100 nm, from 50 nm to 150 nm, from 100 nm to 200 nm, or from 100 nm to 500 nm. In an embodiment, the average pore size of a perforated graphene, graphene-based or two-dimensional material is within the specified range. In embodiments, 70% to 99%, 80% to 99%, 85% to 99% or 90 to 99% of the perforations in a sheet or layer fall within a specified range, but other pores fall outside the specified range.

The technique used for forming the graphene or graphene-based material in the embodiments described herein is not believed to be particularly limited. For example, in some embodiments CVD graphene or graphene-based material can be used. In various embodiments, the CVD graphene or graphene-based material can be liberated from its growth substrate (e.g., Cu) and transferred to a polymer backing, or may be transferred to a porous substrate.

Likewise, the techniques for introducing perforations to the graphene or graphene-based material are not believed to be particularly limited, other than being chosen to produce perforations within a desired size range. Perforations are sized as described herein to provide desired selective permeability of a species (atom, molecule, protein, virus, cell, etc.) for a given application. Selective permeability relates to the propensity of a porous material or a perforated two-dimensional material to allow passage (or transport) of one or more species more readily or faster than other species, or to block the other species from passage. Selective permeability allows separation of species which exhibit different passage or transport rates. In two-dimensional materials selective permeability correlates to the dimension or size (e.g., diameter) of apertures and the relative effective size of the species. Selective permeability of the perforations in two-dimensional materials, such as graphene-based materials, can also depend on functionalization of perforations (if any) and the specific species that are to be separated or blocked. Separation of two or more species in a mixture includes a change in the ratio(s) (weight or molar ratio) of the two or more species in the mixture after passage of the mixture through a perforated two-dimensional material.

Graphene-based materials include, but are not limited to, single layer graphene, multilayer graphene or interconnected single or multilayer graphene domains and combinations thereof. In an embodiment, graphene-based materials also include materials which have been formed by stacking single layer or multilayer graphene sheets. In embodiments, multilayer graphene includes 2 to 20 layers, 2 to 10 layers or 2 to 5 layers. In embodiments, graphene is the dominant material in a graphene-based material. For example, a graphene-based material comprises at least 30% graphene, or at least 40% graphene, or at least 50% graphene, or at least 60% graphene, or at least 70% graphene, or at least 80% graphene, or at least 90% graphene, or at least 95% graphene. In embodiments, a graphene-based material comprises a range of graphene selected from 30% to 95%, from 40% to 80%, from 50% to 70%, from 60% to 95% or from 75% to 100%. In an embodiment, the amount of graphene in the graphene-based material is measured as an atomic percentage.

Graphene represents a form of carbon in which the carbon atoms reside within a single atomically thin sheet or a few layered sheets (e.g., about 20 or less) of fused six-membered rings forming an extended sp2-hybridized carbon planar lattice. Graphene-based materials include, but are not limited to, single layer graphene, multilayer graphene or interconnected single or multilayer graphene domains and combinations thereof. In embodiments, multilayer graphene includes 2 to 25 layers, 2 to 20 layers, 2 to 10 layers or 2 to 5 layers. In an embodiment, layers of multilayered graphene are stacked, but are less ordered in the z direction (perpendicular to the basal plane) than a thin graphite crystal.

In an embodiment, graphene-based materials also include materials which have been formed by stacking single or multilayer graphene sheets. Multi-layered graphene as referred to herein includes multiple sheets of graphene formed by layering as-synthesized sheets on a substrate. In an embodiment, layers of as-synthesized sheets of graphene which have been stacked in this fashion are less ordered in the z direction than an as-synthesized multilayer graphene sheet. Suitable as-synthesized sheets include sheets of single layer graphene (SLG), sheets of bi-layer graphene (BLG) or sheets of few layer graphene (FLG graphene, for example up to 5 layers of graphene). For example, a sheet of single layer graphene (SLG) is layered via float-down on top of a substrate. Another sheet of the SLG is then floated down on the already prepared SLG-substrate stack. This would now be 2 layers of "as-synthesized" SLG on top of the substrate. This can be extended to few layer graphene (FLG) or a mixture of SLG and FLG; and can be achieved through transfer methods known to the art. For example, a polymer transfer method can be used to assemble the stack of polymer layers. In some instances a number of layers is intended to refer to that number of separate layers of transferred graphene. In cases where a layer of transferred graphene can have a range of graphene layers (e.g. some regions of the layer are SLG and others are BLG or FLG), the stack has a range of graphene layers. For example, if 5 layers of transferred graphene each have 1 to 5 layers, then regions where the 5 sheets line up with 5 layers, effectively have 25 layers of graphene at that position. Depending on the perforation conditions, the thicker regions of the stack may not perforate. In embodiments, layering of different sheets of graphene results in a desirable membrane for filtration and separation applications.

In an embodiment, a sheet of graphene-based material is a sheet of single or multilayer graphene or a sheet comprising a plurality of interconnected single or multilayer graphene domains. In embodiments, the multilayer graphene domains have 2 to 5 layers or 2 to 10 layers. As used herein, a "domain" refers to a region of a material where atoms are uniformly ordered into a crystal lattice. A domain is uniform within its boundaries, but different from a neighboring region. For example, a single crystalline material has a single domain of ordered atoms. In an embodiment, at least some of the graphene domains are nanocrystals, having domain size from 1 to 100 nm or 10 to 100 nm. In an embodiment, at least some of the graphene domains have a domain size from 100 nm to 1 micron, or from 200 nm to 800 nm, or from 300 nm to 500 nm. "Grain boundaries" formed by crystallographic defects at edges of each domain differentiate between neighboring crystal lattices. In some embodiments, a first crystal lattice may be rotated relative to a second crystal lattice, by rotation about an axis perpendicular to the plane of a sheet, such that the two lattices differ in "crystal lattice orientation."

In an embodiment, the sheet of graphene-based material comprises a sheet of single layer or multilayer graphene or a combination thereof. In an embodiment, the sheet of graphene-based material is a sheet of single layer or multilayer graphene or a combination thereof. In another embodiment, the sheet of graphene-based material is a sheet comprising a plurality of interconnected single or multilayer graphene domains. In an embodiment, the interconnected domains are covalently bonded together to form the sheet.

When the domains in a sheet differ in crystal lattice orientation, the sheet is polycrystalline.

In embodiments, the thickness of the sheet of graphene-based material is from 0.34 to 10 nm, from 0.34 to 5 nm, or from 0.34 to 3 nm. In an embodiment, a sheet of graphene-based material comprises intrinsic or native defects. Intrinsic or native defects are those resulting from preparation of the graphene-based material in contrast to perforations which are selectively or intentionally introduced into a sheet of graphene-based material or a sheet of graphene. Such intrinsic or native defects may include, but are not limited to, lattice anomalies, pores, tears, cracks or wrinkles. Lattice anomalies can include, but are not limited to, carbon rings with other than 6 members (e.g. 5, 7 or 9 membered rings), vacancies, interstitial defects (including incorporation of non-carbon atoms in the lattice), and grain boundaries.

In an embodiment, the layer comprising the sheet of graphene-based material further comprises non-graphenic carbon-based material located on the surface of the sheet of graphene-based material. In an embodiment, the non-graphenic carbon-based material does not possess long range order and may be classified as amorphous. In embodiments, the non-graphenic carbon-based material further comprises elements other than carbon and/or hydrocarbons. Non-carbon elements which may be incorporated in the non-graphenic carbon include, but are not limited to, hydrogen, oxygen, silicon, copper and iron. In embodiments, the non-graphenic carbon-based material comprises hydrocarbons. In embodiments, carbon is the dominant material in non-graphenic carbon-based material. For example, a non-graphenic carbon-based material comprises at least 30% (weight %) carbon, or at least 40% carbon, or at least 50% carbon, or at least 60% carbon, or at least 70% carbon, or at least 80% carbon, or at least 90% carbon, or at least 95% carbon. In embodiments, a non-graphenic carbon-based material comprises a range of carbon selected from 30% to 95%, or from 40% to 80%, or from 50% to 70%. In an embodiment, the amount of carbon in the non-graphenic carbon-based material is measured as an atomic percentage.

Such nanomaterials in which pores are intentionally created will be referred to herein as "perforated graphene," "perforated graphene-based materials" or "perforated two-dimensional materials." The present disclosure is also directed, in part, to perforated graphene, perforated graphene-based materials and other perforated two-dimensional materials containing a plurality of holes of size (or size range) appropriate for a given application. The size distribution of holes may be narrow, e.g., limited to a 1-10% deviation in size or a 1-20% deviation in size. In an embodiment, the characteristic dimension of the holes is selected for the application. For circular holes, the characteristic dimension is the diameter of the hole. In embodiments relevant to non-circular pores, the characteristic dimension can be taken as the largest distance spanning the hole, the smallest distance spanning the hole, the average of the largest and smallest distance spanning the hole, or an equivalent diameter based on the in-plane area of the pore. As used herein, perforated graphene-based materials include materials in which non-carbon atoms have been incorporated at the edges of the pores.

In various embodiments, the two-dimensional material comprises graphene, molybdenum disulfide, or hexagonal boron nitride. In more particular embodiments, the two-dimensional material can be graphene. Graphene according to the embodiments of the present disclosure can include single-layer graphene, multi-layer graphene, or any combination thereof. Other nanomaterials having an extended two-dimensional molecular structure can also constitute the two-dimensional material in the various embodiments of the present disclosure. For example, molybdenum disulfide is a representative chalcogenide having a two-dimensional molecular structure, and other various chalcogenides can constitute the two-dimensional material in the embodiments of the present disclosure. Choice of a suitable two-dimensional material for a particular application can be determined by a number of factors, including the chemical and physical environment into which the graphene or other two-dimensional material is to be terminally deployed.

The process of forming holes in graphene and other two-dimensional materials will be referred to herein as "perforation," and such nanomaterials will be referred to herein as being "perforated." In a graphene sheet an interstitial aperture is formed by each six-carbon atom ring structure in the sheet and this interstitial aperture is less than one nanometer across. In particular, this interstitial aperture is believed to be about 0.3 nanometers across its longest dimension (the center to center distance between carbon atoms being about 0.28 nm and the aperture being somewhat smaller than this distance). Perforation of sheets comprising two-dimensional network structures typically refers to formation of holes larger than the interstitial apertures in the network structure.

Due to the atomic-level thinness of graphene and other two-dimensional materials, it may be possible to achieve high fluid throughput fluxes during separation or filtration processes, even with holes that are in the ranges of 1-200 nm, 1-100 nm, 1-50 nm, or 1-20 nm.

Chemical techniques can be used to create holes in graphene and other two-dimensional materials. Exposure of graphene or another two-dimensional material to ozone or atmospheric pressure plasma (e.g., an oxygen/argon or nitrogen/argon plasma) can effect perforation. Other techniques, such as ion bombardment, can also be used to remove matter from the planar structure of two-dimensional materials in order to create holes. All such methods can be applied for preparation of perforated two-dimensional materials for use herein dependent upon the hole sizes or range of hole sizes desired for a given application.

In various embodiments of the present disclosure, the holes produced in the graphene or other two-dimensional material can range from about 0.3 nm to about 50 nm in size. In a more specific embodiment, hole sizes can range from 1 nm to 50 nm. In a more specific embodiment, hole sizes can range from 1 nm to 10 nm. In a more specific embodiment, hole sizes can range from 5 nm to 10 nm. In a more specific embodiment, hole sizes can range from 1 nm to 5 nm. In a more specific embodiment, the holes can range from about 0.5 nm to about 2.5 nm in size. In an additional embodiment, the hole size is from 0.3 to 0.5 nm. In a further embodiment, the hole size is from 0.5 to 10 nm. In an additional embodiment, the hole size is from 5 nm to 20 nm. In a further embodiment, the hole size is from 0.7 nm to 1.2 nm. In an additional embodiment, the hole size is from 10 nm to 50 nm. In embodiments where larger hole sizes are preferred, the hole size is from 50 nm to 100 nm, from 50 nm to 150 nm, or from 100 nm to 200 nm.

In general, the terms and phrases used herein have their art-recognized meaning, which can be found by reference to standard texts, journal references and contexts known to those skilled in the art. The following definitions are provided to clarify their specific use in the context of the invention.

As used herein, the term "two-dimensional material" will refer to any extended planar structure of atomic thickness, including both single- and multi-layer variants thereof. Multi-layer two-dimensional materials can include up to about 20 stacked layers.

A "defect" refers to an opening in a plane of a two-dimensional material. In an embodiment, the defect may be an intrinsic or native defect. Intrinsic or native defects are those resulting from preparation of the two-dimensional material in contrast to perforations which are selectively introduced into a sheet of two-dimensional material. Such intrinsic or native defects include, but are not limited to, lattice anomalies, pores, tears, cracks or wrinkles. Lattice anomalies can include, but are not limited to, carbon rings with other than 6 members (e.g. 5, 7 or 9 membered rings) in graphene or graphene-based materials, vacancies, interstitial defects (including incorporation of non-carbon atoms in the lattice), and grain boundaries. In an embodiment, the defect may be a non-intrinsic defect. Non-intrinsic defects are nanoscale apertures (e.g., pores, holes) formed by a defect formation process, wherein energy (e.g., heat, pressure, electromagnetic radiation and combinations and variations thereof) sufficient to break the chemical bonds of the two-dimensional material is applied to at least one target location of the material. A plurality of non-intrinsic defects may be provided in a uniform or non-uniform (i.e., random) distribution or pattern. Typically, non-intrinsic defects are produced in at a target location of a two-dimensional material with precision of ±50 nm, ±10 nm or ±5 nm. In some embodiments, nanoscale apertures in a two-dimensional material are separated by an average closest edge-to-edge distance less than or equal to 20 nm or less than or equal to 15 nm or less than or equal to 10 nm.

A defect healing process, as used herein, refers to a process for partially or completely closing one or more openings (defects) in a two-dimensional material. A defect healing process may transform a perforated two-dimensional material into a less perforated or unperforated two-dimensional material using chemical techniques (e.g., bonding), physical techniques (e.g., blocking) or a combination of chemical and physical techniques. Exemplary healing techniques include, but are not limited to, reforming the crystallographic lattice of the two-dimensional material within the defect area, filling the defect with a material other than the two-dimensional material (e.g., epoxy), and covering the defect with a section of the same or different material, which at least partially overlaps the two-dimensional material. In an embodiment, the process of reforming the crystallographic lattice of the two-dimensional material within the defect area utilizes hydrocarbon-based surface contamination that is mobilized by the addition of energy. In an embodiment, the healing may be performed via a reorganization of existing defects without adding any new material.

"In situ" methods of the present invention are performed on a sample that remains in position throughout the method. For example, a sample that remains "in position" is stationary or does not leave a sample chamber during the in situ method. In situ methods according to the inventive concepts disclosed herein are useful for providing data indicative of a spatial and/or temporal change of a sample that remains in its original position. In some embodiments, an in situ method processes (e.g., perforates or heals) the sample and simultaneously interrogates the sample to provide substantially instantaneous, real-time data. In some embodiments, an in situ method processes (e.g., perforates or heals) the sample and performs nearly simultaneously interrogation of the sample to provide substantially near real-time data.

As described above, the incident radiation, and the scattered, emitted or transmitted radiation may be any one or more of electromagnetic radiation, electrons, ions, nanoparticles, or plasma. In an embodiment, incident radiation is processing radiaton, such as perforating or healing radiation or interrogating radiation. The incident radiation may also be both processing radiation and interrogating radiation. As described herein, processing radiation performs a process on the material when incident thereon.

In some embodiments, the incident perforating or healing radiation may also be interrogating radiation, which interacts with the two-dimensional material to produce scattered, emitted or transmitted radiation that is detected by a detector to provide data indicative of defect formation or healing. In an embodiment, the incident perforating or healing radiation is separate from interrogating radiation, which is produced by an alternate source and which interacts with the two-dimensional material to produce scattered, emitted or transmitted radiation that is detected by a detector to provide data indicative of defect formation or healing.

In an embodiment, the incident radiation does not perforate the two-dimensional material. The incident non-perforating radiation may interrogate the two-dimensional material by interacting with the two-dimensional material to produce scattered, emitted or transmitted radiation that is detected by a detector to provide data indicative of defect formation or healing.

In some embodiments, especially for methods configured for local sampling, micromechanical shutters disposed between the two-dimensional material and the detector could be opened and closed to allow for targeted sampling. Activation of the micromechanical shutters could be implemented by each shutter being biased to collect current from a respective local portion of the material. In an embodiment, the shutters may be arranged in an array over the two dimensional material, each shutter corresponding to a respective local portion. Thus, the respective local portion of the material may be electronically monitored by actuating its respective shutter to open to allow for appropriate radiation to be incident on the respective portion, and the electrical conductivity data of the local portion may be acquired. The shutters may be electrostatically actuated. When the emitted current divided by the bias current is not equal to 1, the actuator may move because the charge on the shutter moves the shutter by coulombic force. Other ways of moving the actuator once the appropriate signal is received are contemplated. In an embodiment, the shutters may be arranged in a two-dimensional array. In another embodiment, the shutters may be arranged in a one-dimensional array.

In some embodiments, probes, such as wires, could be contacted with respective local portions of the two-dimensional material to acquire electrical conductivity data. Thus, the electrical conductivity of the respective local portions may be monitored.

In embodiments, the two-dimensional material is a graphene-based material. In embodiments, the two-dimensional material is graphene.

In embodiments, at least a portion of the holes in the two-dimensional material are functionalized.

Additionally, the conductive properties of graphene-based or other two-dimensional membranes can allow for electrification to take place from an external source. In exemplary embodiments, an AC or DC voltage can be applied to conductive two-dimensional materials.

In some embodiments, the two-dimensional material, such as graphene, can be affixed to a suitable porous substrate. Suitable porous substrates can include, for example, thin film polymers and ceramics. Useful exemplary ceramics include nanoporous silica or SiN. Useful porous polymer substrates include track-etched polymers, expanded polymers or non-woven polymers. The substrate material can be porous or permeable.

FIG. 1 shows a graphene sheet 10 of carbon atoms defining a repeating pattern of hexagonal ring structures that collectively form a two-dimensional honeycomb lattice. An interstitial aperture 12 of less than 1 nm in diameter is formed by each hexagonal ring structure in the sheet. More particularly, the interstitial aperture in a perfect crystalline graphene lattice is estimated to be about 0.23 nanometers across its longest dimension. Accordingly, graphene materials preclude transport of any molecule across the graphene sheet's thickness unless there are pores, perforation-induced or intrinsic. The thickness of a theoretically perfect single graphene sheet is approximately 0.3 nm. Further, graphene has a breaking strength about 200 times that of steel, a spring constant in the range 1 N/m to 5 N/m and a Young's modulus of about 0.5 TPa.

Figure 2:
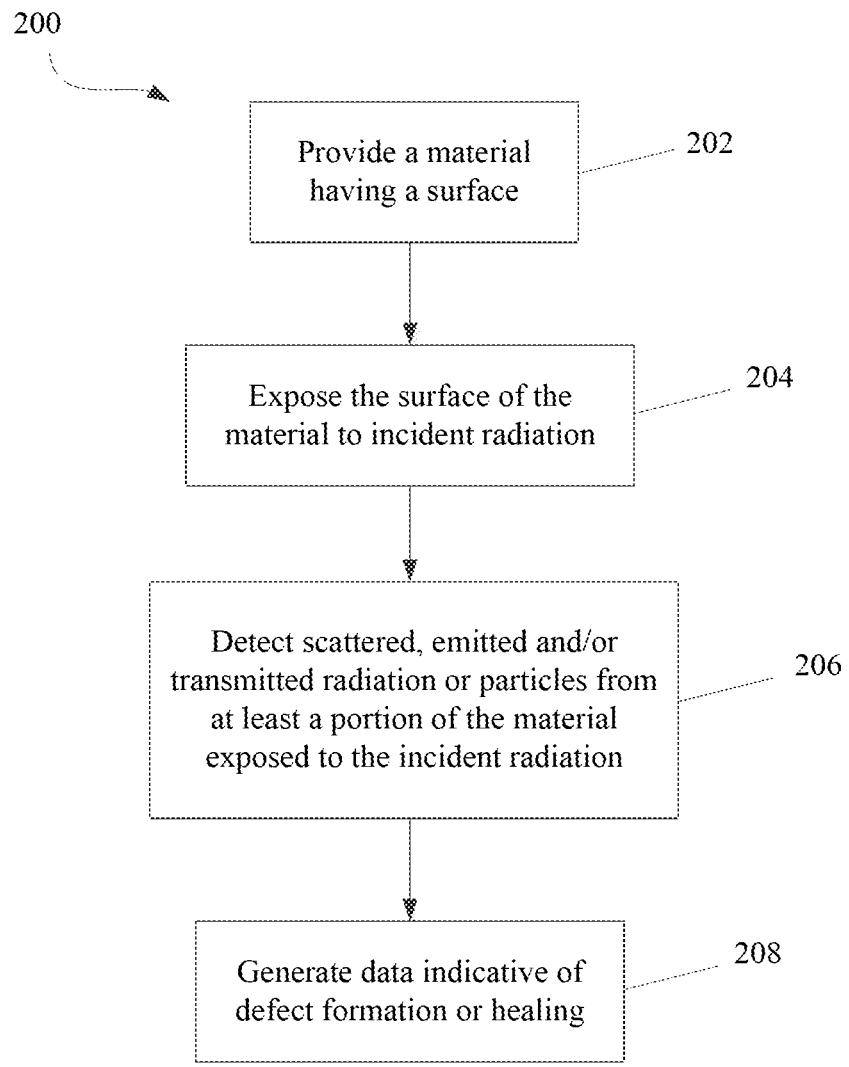
FIG. 2 shows a flowchart for a method for monitoring defect formation or healing via detection of scattered, emitted or transmitted radiation or particles, according to an embodiment of the present invention.

FIG. 2 shows a flowchart 200 for a method for monitoring defect formation or healing via detection of scattered, emitted or transmitted radiation, according to an embodiment of the inventive concepts disclosed herein. Step 202 involves providing a material having a surface. In step 204, the surface of the material is exposed to incident radiation. In step 206, scattered, emitted or transmitted radiation are detected from at least a portion of the material exposed to the incident radiation, and in step 208 data indicative of defect formation or healing is generated. Typically, the method is performed in situ and the data indicative of defect formation or healing provide a rate of defect formation or healing, a temporal change in the rate of defect formation or healing, a temporal change in the size of the defects, a spatial change in the rate of defect formation or healing, a spatial change in the size of the defects, or combinations thereof.

Figure 3:
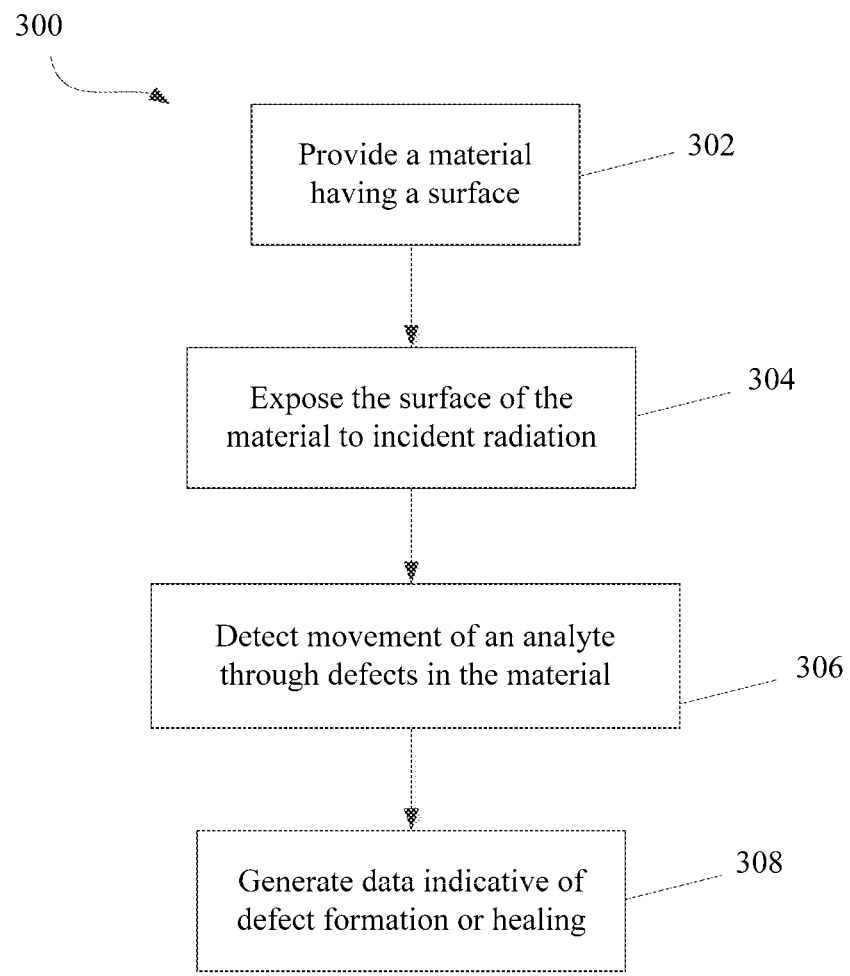
FIG. 3 shows a flowchart for a method for monitoring defect formation or healing via detection of movement of an analyte, according to an embodiment of the present invention.

FIG. 3 shows a flowchart 300 for a method for monitoring defect formation or healing via detection of movement of an analyte, according to an embodiment according to inventive concepts disclosed herein. Step 302 involves providing a material having a surface. In step 304, the surface of the material is exposed to incident radiation. In step 306, movement of an analyte through defects in the material is detected, and in step 308 data indicative of defect formation or healing is generated. Typically, the method is performed in situ and the data indicative of defect formation or healing provide a rate of defect formation or healing, a temporal change in the rate of defect formation or healing, a temporal change in the size of the defects, a spatial change in the rate of defect formation or healing, a spatial change in the size of the defects, a maximum size of the defects, or combinations thereof.

Figure 4:
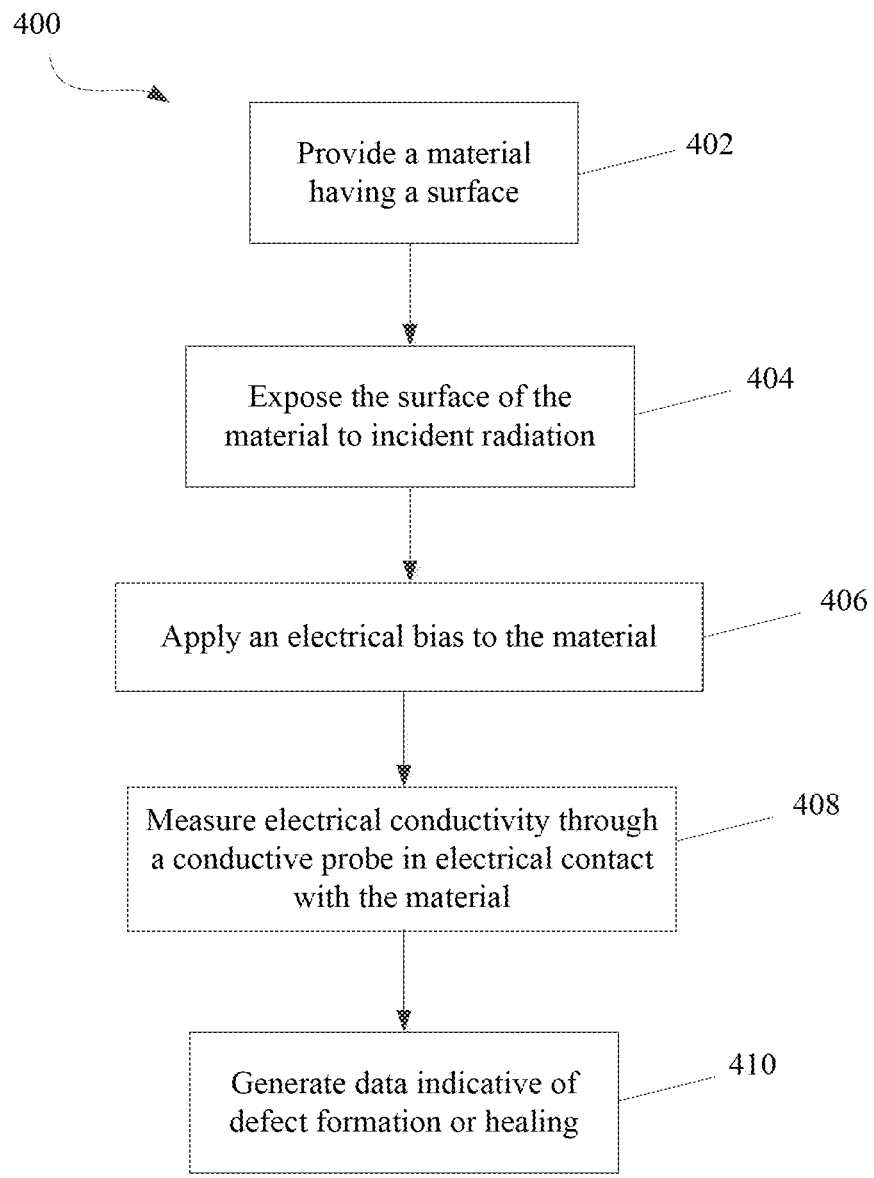
FIG. 4 shows a flowchart for a method for monitoring defect formation or healing via measurement of electrical conductivity, according to an embodiment of the present invention.

FIG. 4 shows a flowchart 400 for a method for monitoring defect formation or healing via measurement of electrical conductivity, according to an embodiment according to inventive concepts disclosed herein. In step 402, a material having a surface is provided and in step 404 the surface of the material is exposed to incident radiation. In step 406, an electrical bias is applied to the material. In step 408, electrical conductivity is measured with a conductive probe in electrical contact with the material. In step 410, data indicative of defect formation or healing is generated. Typically, the method is performed in situ and the data indicative of defect formation or healing provide a rate of defect formation or healing, a temporal change in the rate of defect formation or healing, a temporal change in the size of the defects, a spatial change in the rate of defect formation or healing, a spatial change in the size of the defects, or combinations thereof. In an embodiment, a conductive probe is a conductive grid or a local probe. In an embodiment, defect density and electrical conductivity are inversely related such that an increase in defect density is observed as a decrease in electrical conductivity.

Figure 5:
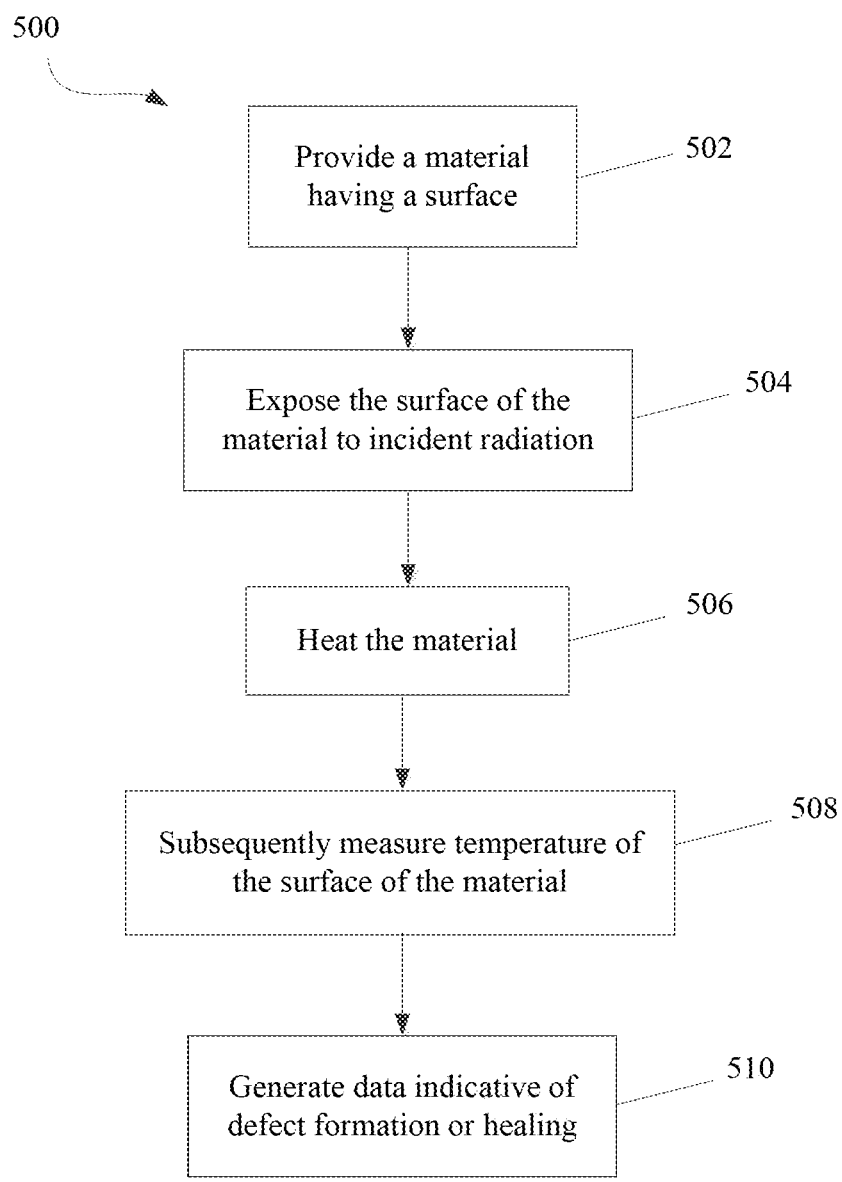
FIG. 5 shows a flowchart for a method for monitoring defect formation or healing via Joule heating and temperature measurement, according to an embodiment of the present invention.

FIG. 5 shows a flowchart 500 for a method for monitoring defect formation or healing via Joule heating and temperature measurement, according to an embodiment according to inventive concepts disclosed herein. In step 502, a material having a surface is provided and the surface of the material is exposed to incident radiation, in step 504. In step 506, the material is heated. Subsequently, temperature of the surface of the material is measured in step 508. In step 510, data indicative of defect formation or healing is generated. Typically, the method is performed in situ and the data indicative of defect formation or healing provides a rate of defect formation or healing, a temporal change in the rate of defect formation or healing, a temporal change in the size of the defects, a spatial change in the rate of defect formation or healing, a spatial change in the size of the defects, or combinations thereof. In an embodiment, the step of heating the material comprises applying a potential to the two-dimensional material to induce joule heating. In an embodiment, defect density and thermal conductivity are inversely related such that an increase in defect density is observed as a decrease in thermal conductivity.

Figure 6A:
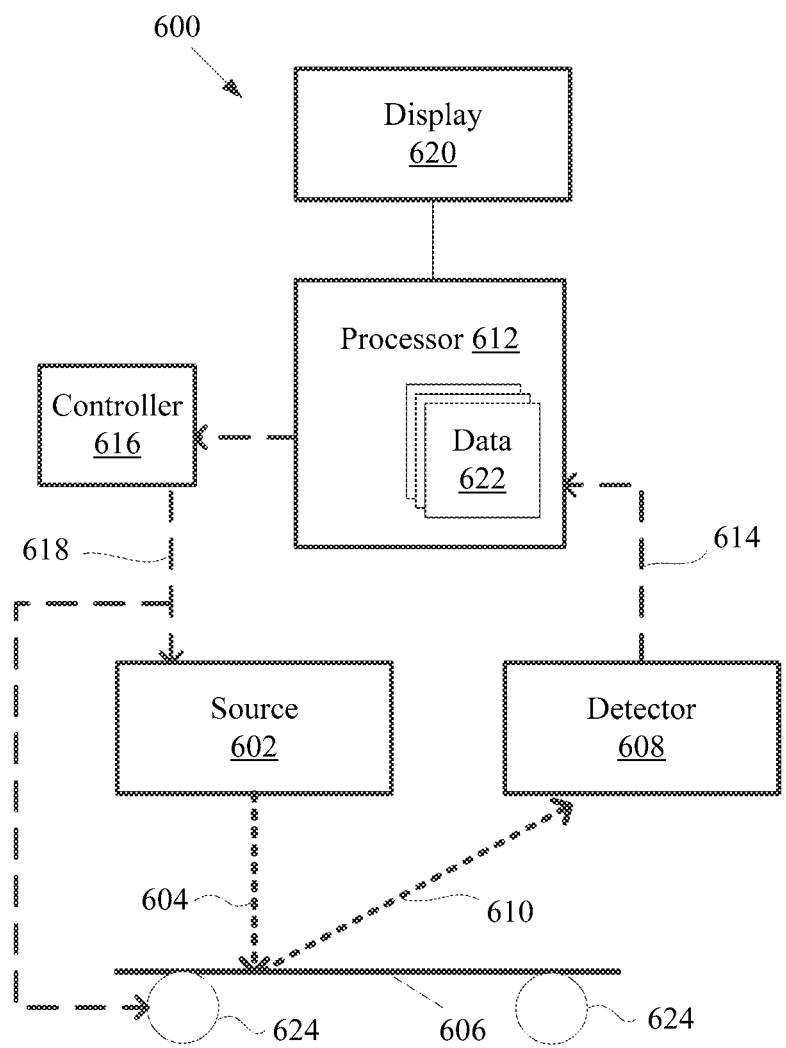
FIGS. 6A and 6B show schematics of exemplary systems for monitoring defect formation or healing, according to the embodiments of the present invention.
Figure 6B:
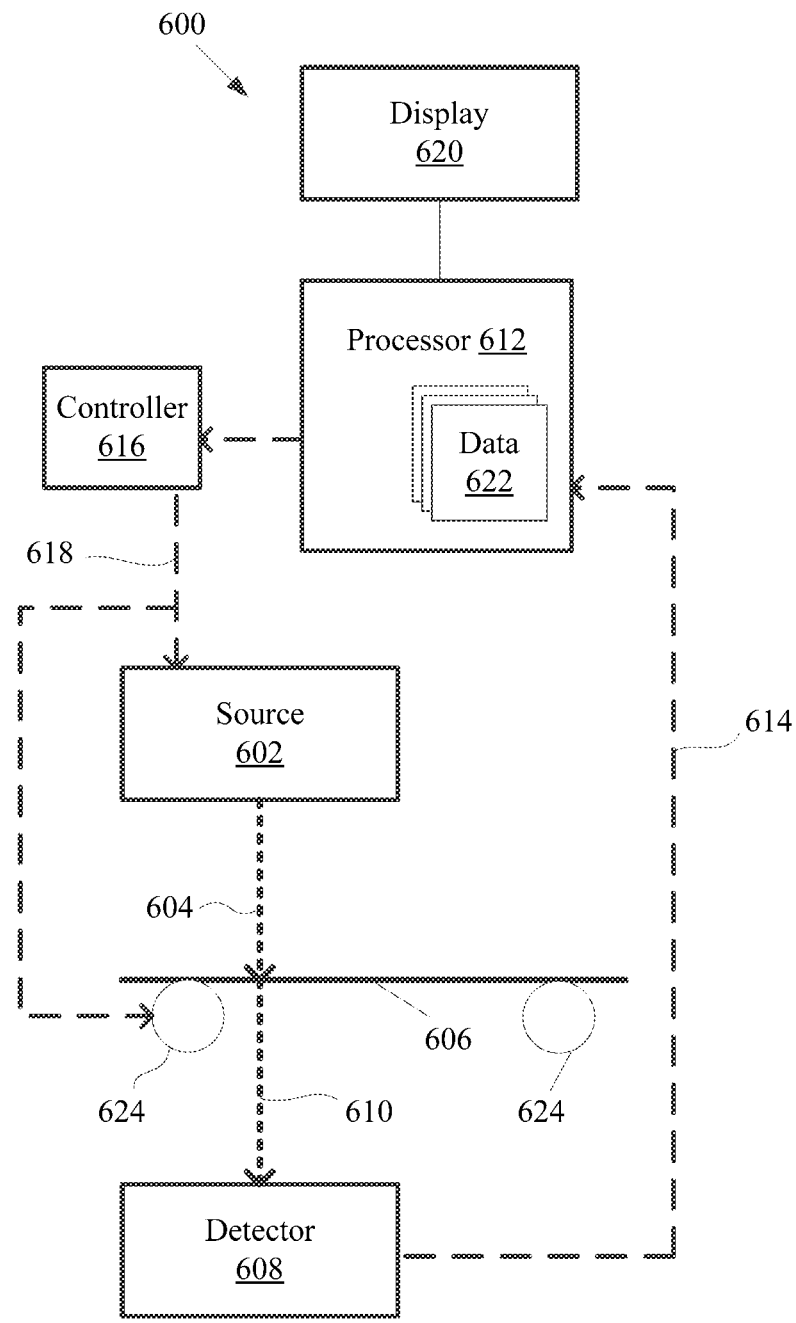

In embodiments, examples of which are schematically illustrated in FIGS. 6A and 6B, a system 600 for monitoring a two-dimensional material comprises a source 602 for delivering incident radiation 604 to a two-dimensional material 606, a detector 608 for receiving scattered, emitted or transmitted radiation or particles 610 from the two-dimensional material 606, and a processor 612 for receiving at least one signal 614 from the detector 608 and transforming the signal 614 into data indicative of defect formation or healing 622. The data 622 may be stored in a register or memory of the processor. In the embodiment shown in FIG. 6A, the detector 608 is positioned on the same side of the two-dimensional material 606 as the source 602 to receive scattered or emitted radiation or particles 610. In the embodiment shown in FIG. 6B, the detector 608 is positioned on the opposite side of the two-dimensional material 606 relative to the source 602 so that the detector 608 can receive transmitted radiation or particles 610. In an embodiment (not shown), a system 600 may include two or more detectors 608 positioned on one or both sides of the two-dimensional material 606. Optionally, the system 600 may also include a controller 616 that receives input 617 from the processor and provides control signals 618 to adjust the incident radiation 604 or a rate of sample translation in response to the data indicative of defect formation or healing 622 and/or a display 620 for visualizing the data. The rate of sample translation may be controlled by translation means, such as rollers 624 and/or a translation stage. Those of skill in the art will appreciate that for some methods disclosed herein the detector may be located on the same side of the two-dimensional material as the incident radiation source. Such configurations typically utilize detectors that are off-axis between about 15° and 75° relative to the trajectory of the incident radiation beam in order to protect the detector from damage. However, other methods disclosed herein may include a detector located on the opposite side of the two-dimensional material from the incident radiation source. Detectors that may be used in the methods disclosed herein include, but are not limited to, electron detectors, mass spectrometers, electromagnetic spectrometers, microbalances, Faraday cups, charge-coupled devices, ion detectors, resistors, capacitors, thermocouples, microchannel plates, phosphor screens, photodiodes and thermistors.

Inventive concepts disclosed herein will now be described with reference to the following non-limiting example.

EXAMPLE

In Situ Monitoring of Graphene Defect Formation or Healing

Suspended graphene on a substrate is loaded into an ion chamber on a platen and pumped down to $10^{-6}$-$10^{-7}$ Torr while being heated to 50° C. Once the pressure is achieved the ion source (Kaufman source), which is a $Xe^+$ beam of approximately 1 mm diameter at 300V and a beam current of 100 nA/mm$^2$ (6.24×10$^{13}$ $Xe^+$/cm$^2$·s), is rastered across the sample. The beam dwells such that the FWHM of the beam profile touches the previous dwell location. The dwell time for each spot is determined by monitoring the secondary electron (SE) emission from the incoming $Xe^+$ using an Everhart-Thornley detector and is compared to known yields (defined as SE emitted for given incident ions in this case) for a given desired pore size, on a particular substrate, with these conditions (i.e. ion voltage, flux, etc.) which were previously acquired empirically. Once the proper SE electron yield is achieved (e.g., actual values match target values on a look-up table), a processor of the control system sends instructions to the instrument to move the beam to the next defect or healing location. The system also accounts for changes in expected yield over time as irradiation progresses.

Statements Regarding Incorporation by Reference and Variations

Although devices and methods have been described with reference to the disclosed embodiments, one having ordinary skill in the art will readily appreciate that these are only illustrative. It should be understood that various modifications can be made without departing from the spirit of the disclosure. The disclosure can be modified to incorporate any number of variations, alterations, substitutions or equivalent arrangements not heretofore described, but which are commensurate with the spirit and scope of the disclosure. Additionally, while various embodiments have been described, it is to be understood that aspects of the disclosure may include only some of the described embodiments. Accordingly, the disclosure is not to be seen as limited by the foregoing description.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomer and enantiomer of the compound described individually or in any combination. One of ordinary skill in the art will appreciate that methods, device elements, starting materials and synthetic methods other than those specifically exemplified can be employed in the practice of the invention without resort to undue experimentation. All art-known functional equivalents, of any such methods, device elements, starting materials and synthetic methods are intended to be included in this invention. Whenever a range is given in the specification, for example, a temperature range, a time range, or a composition range, all intermediate ranges and subranges, as well as all individual values included in the ranges given are intended to be included in the disclosure. When a Markush group or other grouping is used herein, all individual members of the group and all combinations and subcombinations possible of the group are intended to be individually included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The inventive concepts illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The preceding definitions are provided to clarify their specific use in the context of the invention.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claims.

What is claimed is:

1. A method for monitoring defect formation or healing, comprising:
   exposing a surface of a material to incident radiation, the material being a two-dimensional material including a graphene or graphene-based film;
   detecting scattered, emitted and/or transmitted radiation from at least a portion of the material exposed to the incident radiation; and
   generating data indicative of defect formation or healing, wherein the method is performed in situ where the defect formation or healing occurs and the data indicative of defect formation or healing provide a rate of defect formation or healing, a temporal change in the rate of defect formation or healing, a temporal change in the size of the defects, a spatial change in the rate of defect formation or healing, a spatial change in the size of the defects, or combinations thereof.

2. The method of claim 1, wherein the step of exposing the surface of the material to incident radiation produces a plurality of defects in the material.

3. The method of claim 1, wherein the step of detecting radiation or particles comprises:
   (i) performing secondary ion mass spectroscopy;
   (ii) performing Raman spectroscopy;
   (iii) performing residual gas analysis on particles being removed from the material;
   (iv) detecting back scattered radiation or particles;
   (v) detecting Auger electrons;
   (vi) performing scanning probe microscopy;
   (vii) performing scanning tunneling microscopy;
   (viii) performing atomic force microscopy;
   (ix) performing X-ray photoelectron spectroscopy;
   (x) performing transmission electron microscopy;
   (xi) detecting nanoparticles on one or more microbalances or Faraday cups positioned behind the material;
   (xii) performing small angle electron diffraction;
   (xiii) detecting nanoparticles on a surface positioned behind the material using surface enhanced Raman scattering (SERS);
   (xiv) detecting secondary electrons;
   (xv) detecting transmitted electron or ions; or
   (xvi) performing a combination of two or more of (i)-(xv).

4. The method of claim 3, wherein the back scattered radiation are selected from the group consisting of electrons, protons, helium, gallium, neon, argon, xenon or ions.

5. The method of claim 1, wherein the step of generating data indicative of defect formation comprises determining secondary electron yield.

6. The method of claim 1, wherein the steps of exposing and detecting occur simultaneously.

7. The method of claim 1, wherein the incident radiation is perforating radiation, interrogating radiation or both.

8. The method of claim 1, wherein the incident radiation and the scattered, emitted and/or transmitted radiation are the same type of radiation or different types of radiation.

9. The method of claim 1, wherein the scattered, emitted or transmitted radiation results from the incident radiation or an additional source of interrogating radiation.

10. The method of claim 1, wherein the scattered, emitted and/or transmitted radiation from the material is collected from a bulk portion of the surface having an area between 1 $\mu m^2$ and 100 $cm^2$.

11. The method of claim 1, wherein the scattered, emitted and/or transmitted radiation from the material is collected from a local portion of the surface having an area between 100 nm$^2$ and 10 mm$^2$.

12. The method of claim 1, wherein the scattered, emitted and/or transmitted radiation is continuously collected.

13. The method of claim 1, wherein the incident radiation is pulsed, perforating radiation and the scattered, emitted and/or transmitted radiation is collected only when the incident radiation is off.

14. The method of claim 1, wherein the emitted radiation is secondary electrons.

15. A method for monitoring defect formation or healing, comprising:
    exposing a surface of a material to incident radiation, the material being a two-dimensional material including a graphene or graphene-based film;
    detecting movement of an analyte through defects in the material; and
    generating data indicative of defect formation or healing, wherein the method is performed in situ where the defect formation or healing occurs and the data indicative of defect formation or healing provide a rate of defect formation or healing, a temporal change in the rate of defect formation or healing, a temporal change in the size of the defects, a spatial change in the rate of defect formation or healing, a spatial change in the size of the defects, a maximum size of the defects, or combinations thereof.

16. The method of claim 15, wherein the step of detecting movement of the analyte through the defects in the material comprises one or more of:
    (i) determining the presence or absence of the analyte at a detector;
    (ii) quantifying the analyte;
    (iii) identifying a composition, mass, average radius, charge or size of the analyte;
    (iv) determining a rate of movement of the analyte through the defects in the material; or
    (v) a combination of two or more of (i)-(iv).

17. The method of claim 15, wherein the analyte is a gas selected from the group consisting of hydrogen, helium, oxygen, nitrogen, xenon, neon, argon, SF$_6$, H$_2$O, C$_x$H$_{2x}$ where x is 1 to 4, and combinations thereof.

18. The method of claim 15, wherein the analyte is a plasma.

19. The method of claim 15, wherein the incident radiation is a plasma and the analyte is one or more species of the plasma.

20. A method for monitoring defect formation or healing, comprising:
    exposing a surface of a material to incident radiation;
    applying an electrical bias to the material, the material being a two-dimensional material including a graphene or graphene-based film;
    measuring electrical conductivity through a conductive probe in electrical contact with the material; and
    generating data indicative of defect formation or healing, wherein the method is performed in situ where the defect formation or healing occurs and the data indicative of defect formation or healing provide a rate of defect formation or healing, a temporal change in the rate of defect formation or healing, a temporal change in the size of the defects, a spatial change in the rate of defect formation or healing, a spatial change in the size of the defects, or combinations thereof.

21. A method for monitoring defect formation or healing, comprising:
    exposing a surface of a material to incident radiation, the material being a two-dimensional material including a graphene or graphene-based film;
    heating the material;
    subsequently measuring temperature of the surface of the material; and
    generating data indicative of defect formation or healing, wherein the method is performed in situ where the defect formation or healing occurs and the data indicative of defect formation or healing provide a rate of defect formation or healing, a temporal change in the rate of defect formation or healing, a temporal change in the size of the defects, a spatial change in the rate of defect formation or healing, a spatial change in the size of the defects, or combinations thereof.

22. The method of claim 1, wherein the incident radiation is a particle beam.

23. The method of claim 22, wherein the particle beam produces a spot on the surface of the material, the spot having an area between 1 μm$^2$ and 100 cm$^2$.

24. The method of claim 22, wherein the particle beam produces a spot on the surface of the material, the spot having an area between 1 nm$^2$ and 10 mm$^2$.

25. The method of claim 22, wherein the particle beam is an ion beam.

26. The method of claim 25, wherein the ion beam has an ion energy of at least 20 eV.

27. The method of claim 25, wherein the ion beam has a flux selected from the range of 10 pA/mm$^2$ to 1 μA/mm$^2$.

28. The method of claim 22, wherein the particle beam is an electron beam.

29. The method of claim 28, wherein the electron beam has an energy of at least 10 eV.

30. The method of claim 22, wherein the particle beam is a nanoparticle beam.

31. The method of claim 30, wherein the nanoparticle beam has an energy of at least 1 keV per nanoparticle.

32. The method of claim 30, wherein the nanoparticle beam has a flux selected from the range of 1.6×10$^5$ nanoparticles/s·cm$^2$ to 1×10$^{15}$ nanoparticles/s·cm$^2$.

33. The method of claim 1, wherein the two-dimensional material is a single atomic layer thick.

34. The method of claim 1, wherein the material comprises a stack of two or more sheets of two-dimensional material, wherein each sheet is a single atomic layer thick.

35. The method of claim 2, wherein the defects are pores having an average characteristic dimension less than or equal to 1 nm.

36. The method of claim 2, wherein the defects are pores having an average characteristic dimension ranging from 0.3 nm to 100 nm.

37. The method of claim 1, further comprising:
    comparing the data indicative of defect formation or healing to a threshold range for the data; and
    adjusting an energy or amount of the incident radiation if the data is outside of the threshold range.

38. The method of claim 1, further comprising translating the material at a rate dependent upon a rate of defect formation or healing.

* * * * *